United States Patent
Hergenrother et al.

(10) Patent No.: US 11,274,106 B2
(45) Date of Patent: Mar. 15, 2022

(54) TOPOISOMERASE INHIBITORS WITH ANTIBACTERIAL AND ANTICANCER ACTIVITY

(71) Applicant: THE BOARD OF TRUSTEES OF THE UNIVERSITY OF ILLINOIS, Urbana, IL (US)

(72) Inventors: Paul J. Hergenrother, Champaign, IL (US); Andrew P. Riley, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/624,335

(22) PCT Filed: Jun. 21, 2018

(86) PCT No.: PCT/US2018/038745
§ 371 (c)(1),
(2) Date: Dec. 19, 2019

(87) PCT Pub. No.: WO2018/237140
PCT Pub. Date: Dec. 27, 2018

(65) Prior Publication Data
US 2020/0123173 A1    Apr. 23, 2020

Related U.S. Application Data

(60) Provisional application No. 62/524,203, filed on Jun. 23, 2017.

(51) Int. Cl.
    *C07D 498/16*    (2006.01)
(52) U.S. Cl.
    CPC .................................. *C07D 498/16* (2013.01)
(58) Field of Classification Search
    CPC .................................................... C07D 498/16
    See application file for complete search history.

(56) References Cited

U.S. PATENT DOCUMENTS

| | | |
|---|---|---|
| 5,668,286 A | 9/1997 | Yamada et al. |
| 5,700,799 A | 12/1997 | Hutchinson et al. |
| 6,686,363 B2 | 2/2004 | Fukuda |
| 9,611,266 B2 | 4/2017 | Hergenrother et al. |
| 2003/0013737 A1 | 1/2003 | Gordeev et al. |
| 2003/0225107 A1 | 12/2003 | Fukuda |
| 2004/0162279 A1 | 8/2004 | Barbachyn et al. |
| 2005/0004174 A1 | 1/2005 | Gordeev et al. |
| 2005/0070526 A1 | 3/2005 | Agarwal et al. |
| 2005/0118624 A1 | 6/2005 | Ma et al. |
| 2007/0167414 A1 | 7/2007 | Agarwal et al. |
| 2010/0069441 A1 | 3/2010 | Gordeev et al. |
| 2011/0245258 A1 | 10/2011 | Jain et al. |
| 2012/0157434 A1 | 6/2012 | Gordeev et al. |
| 2012/0258980 A1 | 10/2012 | Igarashi et al. |
| 2015/0322530 A1 | 11/2015 | Orsulic et al. |
| 2016/0257651 A1 | 9/2016 | Hiramatsu et al. |
| 2017/0096436 A1 | 4/2017 | Hergenrother et al. |

FOREIGN PATENT DOCUMENTS

| | | |
|---|---|---|
| EP | 2130831 A1 | 12/2009 |
| EP | 2500022 B1 | 12/2015 |
| JP | 2004203809 A | 7/2004 |
| WO | 1995007271 A1 | 3/1995 |
| WO | 03093247 A2 | 11/2003 |
| WO | 2006022794 A1 | 3/2006 |
| WO | 2009001192 A3 | 5/2010 |
| WO | 2017017631 A2 | 2/2017 |
| WO | 2017156519 A1 | 9/2017 |

OTHER PUBLICATIONS

Bair et al., "Chemistry and Biology of Deoxynyboquinone, a Potent Inducer of Cancer Cell Death," J. Am. Chem. Soc.,132(15):5469-5478, Mar. 2010.
Bisacchi et al., "A "Double-Edged" Scaffold: Antitumor Power within the Antibacterial Quinolone," Curr Med Chem., 23(6):520-577, Feb. 2016.
Egawa et al., "Deoxynybomycin is a Selective Anti-Tumor Agent Inducing Apoptosis and Inhibiting Topoisomerase I," Biol Pharm Bull., 23(9):1036-1040, Sep. 2000.
Hiramatsu et al., "Curing Bacteria of Antibiotic Resistance: Reverse Antibiotics, A Novel Class of Antibiotics in Nature," Int J Antimicrob Agents, 39(6):478-485, Jun. 2012.
International Search Report and Written Opinion of the ISA/US dated Sep. 14, 2018 in International Application No. PCT/US2018/387458; 6pgs.
Parkinson et al., "Deoxynybomycins Inhibit Mutant DNA Gyrase and Rescue Mice Infected with Fluoroquinolone-Resistant Bacteria," Nature Comm., 6(2947):1-9 Apr. 2015.

(Continued)

*Primary Examiner* — Brian E McDowell
(74) *Attorney, Agent, or Firm* — Haukaas Fortius PLLC; Michael H. Haukaas

(57) ABSTRACT

Herein is described the conversion of deoxynybomycin (DNM), a natural product and DNA gyrase inhibitor with minimal cytotoxicity, into a compound (Formula I) that has anticancer activity. Detailed in vitro and cell culture experiments demonstrate that these compounds inhibit Top2 and also act upon topoisomerase I. Similar approaches are applicable to other classes of gyrase inhibitors and other antibacterial targets for discovery of new anticancer drugs.

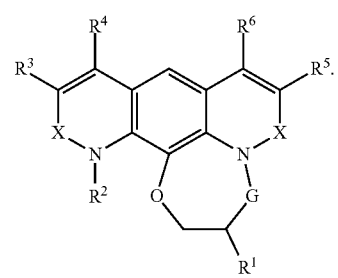

(I)

13 Claims, 12 Drawing Sheets

(56) References Cited

OTHER PUBLICATIONS

Richter et al., "Predictive Compound Accumulation Rules Yield a Broad-Spectrum Antibiotic," Nature, 545:299-304, May 2017.
Richter et al., "Predictive Rules for Compound Accumulation Yield a Broad-Spectrum Antibiotic," Nature, 545(7654):299-304, May 2017.
Chemical Abstracts STN Registry Database, Record for RN 123601-72-9, Nov. 1989.
Gleave et al., "Synthesis and Antibacterial Activity of [6,5, 5] and [6,6, 5] Tricyclic Fused Oxazolidinones," Bioorg Med Chem Lett., 8(10):1231-1236, May 1998.
International Search Report and Written Opinion of the ISA/US dated Jul. 18, 2017 in International Application No. PCT/US2017/022029 ; 14pgs.
Li et al., "Synthesis and Antibacterial Activity of (S)-5-Acetyl Aminomethyl-3-[(4-Substituted-Aminomethyl}phenyl]-2-Oxazolidinone Derivatives," Yao Xue Xue Bao, 41(5):418-425, May 2006.
Naganawa et al., "Deoxynybomycin from a Streptomyces," J Antibiot. (Tokyo), 23(7):365-368, Jul. 1970.
Poel et al., "Antibacterial Oxazolidinones Possessing a Novel C-5 Side Chain. (5R)-trans-3-[3-Fluoro-4-(1-oxotetrahydrothiopyran-4-yl)phenyl]-2-oxooxazolidine-5-carboxylic Acid Amide (PF-00422602), a New Lead Compound," J Med Chem., 50(24):5886-5889, Nov. 2007.
Zhou et al., "Design at the Atomic Level: Generation of Novel Hybrid Biaryloxazolidinones as Promising New Antibiotics," Bioorg Med Chem Lett., 18(23):6179-6183, Dec. 2008.

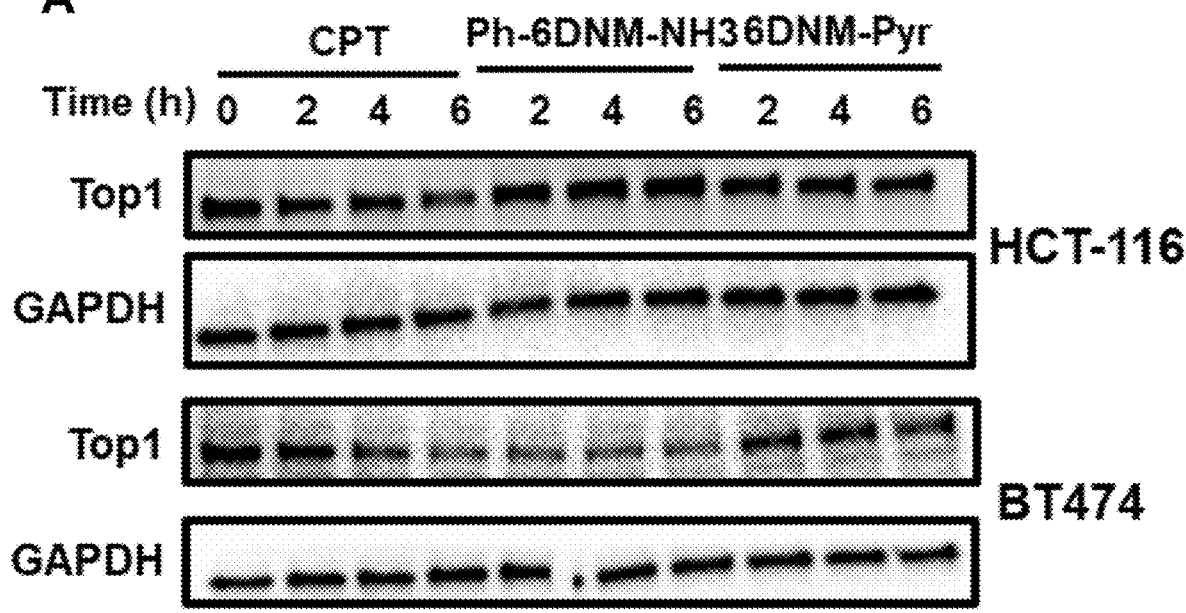
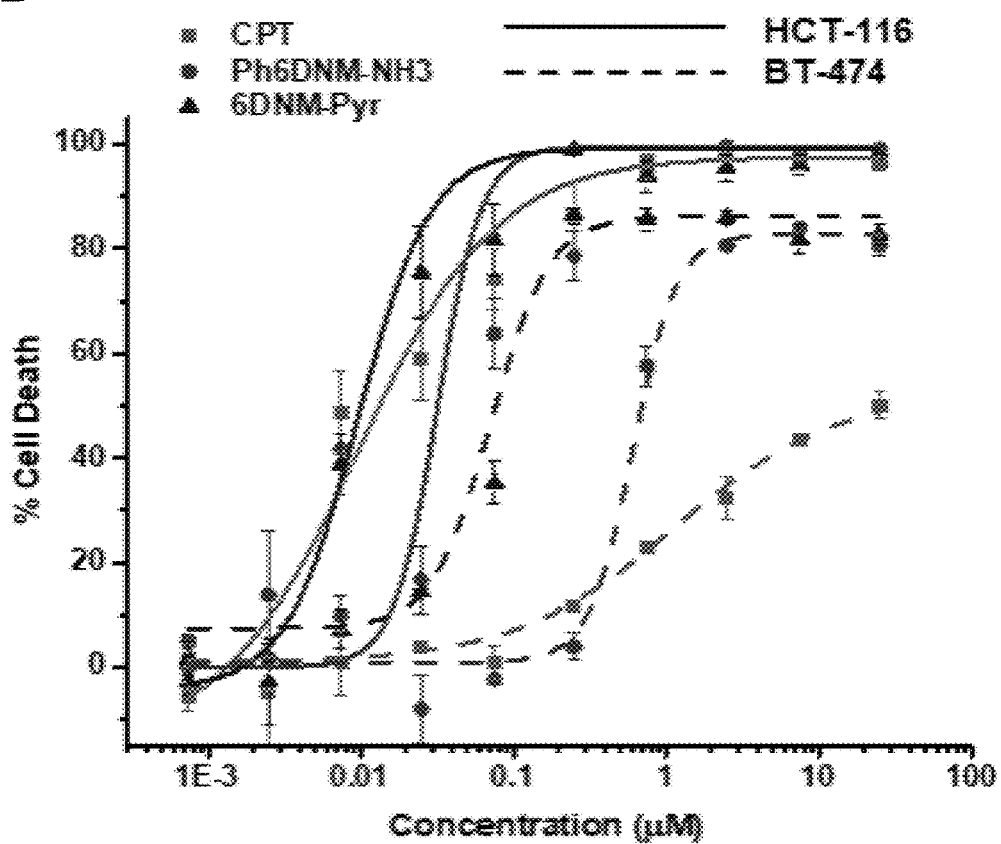
Fig. 4

|  | Top2 | | |
|---|---|---|---|
|  | Poison | Cat. Inhib. | No Activity |
| Top1 No Activity | *Doxorubicin*<br>*Etoposide*<br>*Mitroxone*<br>Vosaroxin | *Dexrazoxane*<br>Merbarone | LEGEND<br><u>DNM Derivative</u><br>*Approved*<br>Clinical Candidate |
| Top1 Cat. Inhib. |  | <u>6DNM-NH3</u><br><u>6DNM-Pyr</u><br>*Aclarubicin*<br>Pyrazoloacridine<br>Tafluposide |  |
| Top1 Poison | DACA<br>XR11576<br>Intoplicine<br>TAS 103<br>Batracylin | <u>Ph-6DNM-NH3</u><br>BN80927 | *Camptothecins*<br>*Irinotecan*<br>Indotecan<br>Endotecarin |

*Fig. 5*

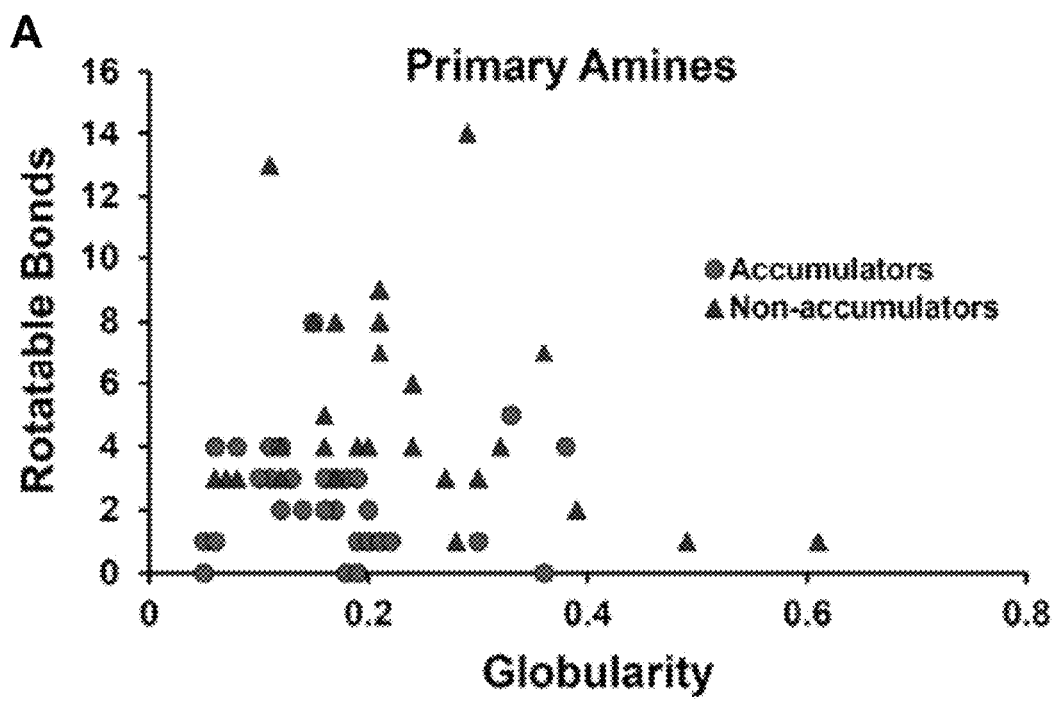
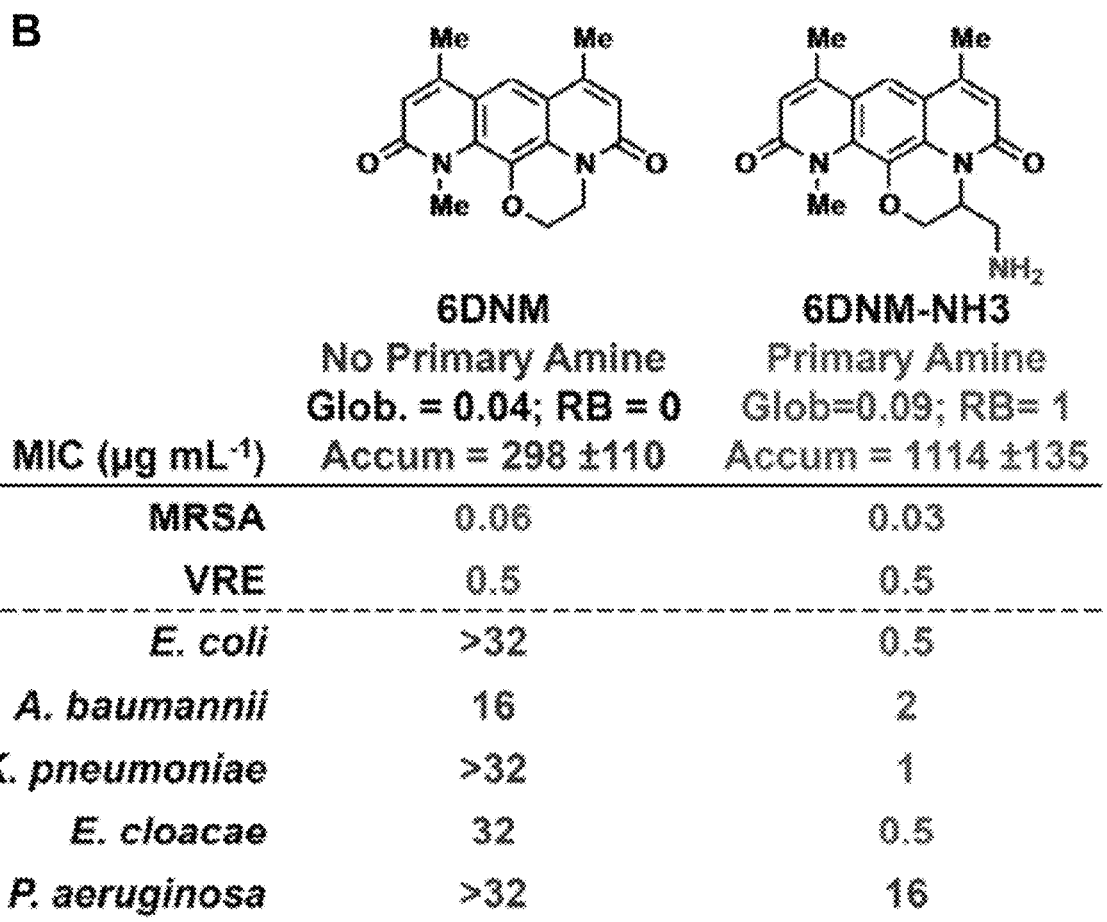
*Fig. 10*

TOPOISOMERASE INHIBITORS WITH ANTIBACTERIAL AND ANTICANCER ACTIVITY

RELATED APPLICATIONS

This application is a National Stage filing under 35 U.S.C. § 371 of International Application No. PCT/US2018/038745, filed Jun. 21, 2018, which claims priority under 35 U.S.C. § 119(e) to U.S. Provisional Patent Application No. 62/524,203, filed Jun. 23, 2017, which applications are incorporated herein by reference.

BACKGROUND OF THE INVENTION

Since the introduction of naldixic acid in 1968, quinolones have remained among the most commonly used classes of antibiotics for a wide range of bacterial infections. Much of this success can be attributed to the ability of quinolones to selectivity target the bacterial type II topoisomerases (DNA gyrase and Topoisomerase IV) despite a high degree of structural and functional homology to the eukaryotic topoisomerase topoisomerase II (Top2). In the 1980s several experimental antibacterial quinolones were identified that also inhibit Top2, which imbues these compounds with significant cytotoxicity and genotoxicity to mammalian cells; as such there is now routine counter-screening for Top2 inhibition when developing novel antibacterial DNA gyrase inhibitors. Despite these precautions, the clastogenic effects of gemifloxacin, a fourth-generation fluoroquinolone, have been attributed to its action at Top2.

Although it represents an off-target liability for antibacterial quinolones, Top2 is a well-validated anticancer target as demonstrated by the broad-utility and wide-scale use of anthracyclines (such as doxorubicin (DOX)), and epipodophyllotoxins (such as etoposide (ETP) and teniposide). For instance, DOX is commonly used to treat cancers of the breast, lung, and ovaries, as well as leukemias, lymphomas, osteosarcomas, and soft tissue sarcomas. Despite their effectiveness, these and other anticancer topoisomerase inhibitors possess severe, often dose-limiting, side-effects including the cardiomyopathy and congestive heart failure associated with DOX treatment. While significant effort has been made to circumvent this cardiotoxicity through liposomal formulations, cardioprotective agents, and the generation of novel anthracyclines, the complexity of the mechanism behind this cardiotoxicity, which likely involves both inhibition of the Top2β isoform and generation of reactive oxygen species (ROS), has prevented a robust solution from emerging. As such, the recommended lifetime cumulative doses of DOX is limited to <500 mg/m² for adults. In addition to anthracycline-induced cardiotoxicity, other Top2-targeting drugs, including etoposide and mitroxone, produce therapy-related acute myeloid leukemia resulting from balanced chromosomal translocations associated with Top2β-dependent double strand breaks.

The discovery of compounds that target eukaryotic topoisomerase thus serendipitously present an opportunity for the development of novel anticancer drugs, work that in an ideal case would result in new Top2 inhibitors not plagued by the side-effects of the current agents in clinical use. Although the generality of such a conversion strategy is unknown, work on vosaroxin, a first-in-class anticancer quinolone currently in clinical development for the treatment of AML and NSCLC suggests considerable promise.

Accordingly, there is a need for a new class of efficacious topoisomerase II inhibitors having a desirable safety profile that can be used to fight illnesses such as those resulting from bacterial infections or cancers.

SUMMARY

This disclosure provides a class of compounds called deoxynybomycins (DNMs), which are antibacterial natural products with impressive activity against drug-resistant Gram-positive bacteria due their ability to inhibit bacterial DNA gyrase with mutations that impart high levels of fluoroquinolone resistance. The DNM core is amenable to structural modification, allowing for the design of DNM analogues with improved solubility and spectrum of activity. Additionally, these unnatural DNMs are well-tolerated in vivo and possess good bioavailability and pharmacokinetic properties. Therefore, anticancer DNMs could overcome the cardiotoxicity liability of the anthracyclines and possess suitable drug-like properties in vivo. Herein is reported the conversion of the natural product antibiotic DNM (FIG. 1) into several highly potent anticancer compounds. Mechanistic studies reveal that in addition to targeting Top2, these DNMs also target Top1 and that subtle changes in structure result in differences in modes of inhibition. Finally, using a syngeneic tumor model it was shown that these results can be quickly translated into in vivo systems, highlighting the power of this approach of developing new classes of anticancer topoisomerase inhibitors based on established antibacterial classes.

Accordingly, this disclosure provides a compound of Formula I:

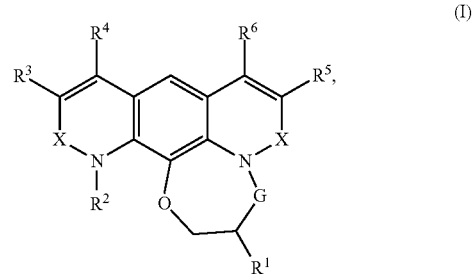

(I)

or a salt or solvate thereof;
wherein
G is a direct bond or $CH_2$;
each X is independently $CH_2$ or C=O;
$R^1$ is H, —($C_1$-$C_6$)alkyl, —$OR^A$, —$SR^A$, —S(=O)$_2$N($R^A$)$_2$, —N($R^A$)$_2$, —($C_1$-$C_5$)alkyl-$OR^A$, —($C_1$-$C_5$)alkyl-$SR^A$, —($C_1$-$C_5$)alkyl-S(=O)$_2$N($R^A$)$_2$, —($C_1$-$C_5$)—N($R^A$)$_2$, or —($C_1$-$C_5$)alkyl-C(=O)$R^B$;
$R^2$ is H, —($C_1$-$C_6$)alkyl, or —($C_3$-$C_6$)cycloalkyl;
each $R^3$ and $R^4$ are independently H, —($C_1$-$C_6$)alkyl, or $R^3$ and $R^4$ taken together form a cycloalkyl or an aryl;
each $R^5$ and $R^6$ are independently H, —($C_1$-$C_6$)alkyl, or $R^5$ and $R^6$ taken together form a cycloalkyl or an aryl;
$R^A$ is H, —($C_1$-$C_6$)alkyl, —($C_3$-$C_6$)cycloalkyl, or —C(=O)$R^B$; and
$R^B$ is H, —($C_1$-$C_6$)alkyl, —OH, or —$NH_2$;
wherein each —($C_1$-$C_6$)alkyl, —($C_3$-$C_6$)cycloalkyl and aryl are optionally substituted with one or more substituents and optionally both $R^A$ in —N($R^A$)$_2$ taken together form a 5- or 6-membered heterocycle.

The invention provides novel compounds of Formulas I-IV, intermediates for the synthesis of compounds of Formulas I-IV, as well as methods of preparing compounds of Formulas I-IV. The invention also provides compounds of Formulas I-IV that are useful as intermediates for the synthesis of other useful compounds. The invention provides for the use of compounds of Formulas I-IV for the manufacture of medicaments useful for the treatment of bacterial infections in a mammal, such as a human.

The invention provides for the use of the compositions described herein for use in medical therapy. The medical therapy can be treating cancer, for example, breast cancer, lung cancer, ovarian cancer, or cervical cancer. The invention also provides for the use of a composition as described herein for the manufacture of a medicament to treat a disease in a mammal, for example, cancer in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 4. Level of Top1-degradation predicts cell line sensitivity. (a) Cells treated with 25 µM of compound for indicated times followed by a 30 minute incubation with drug-free media. Cells were lysed with RIPA and Top1 levels assessed by Western Blot. (b) Degradation of Top1 results in a right-ward shift in the dose-response curve. Effect is most pronounced in Top1-poisons (Ph-6DNM-NH3, CPT) than Top1 catalytic inhibitor (6DNM-Pyr). Cell death measured by SRB assay after 72 hour of compound exposure (n≥3 biological replicates, error bars show SEM).

FIG. 5. The modes of topoisomerase inhibition for DNM derivatives (underlined) compared to topoisomerase-targeting drugs representative of drug-classes approved (italicized) or under clinical development (bolded) for the treatment of cancer.

FIG. 10. Conversion of DNM into broad-spectrum agent. Guidelines for Gram-negative accumulation: 1) Compound contains a primary amine; 2) globularity<0.25; 3) rotatable bonds <5.

DETAILED DESCRIPTION

Figure 1:
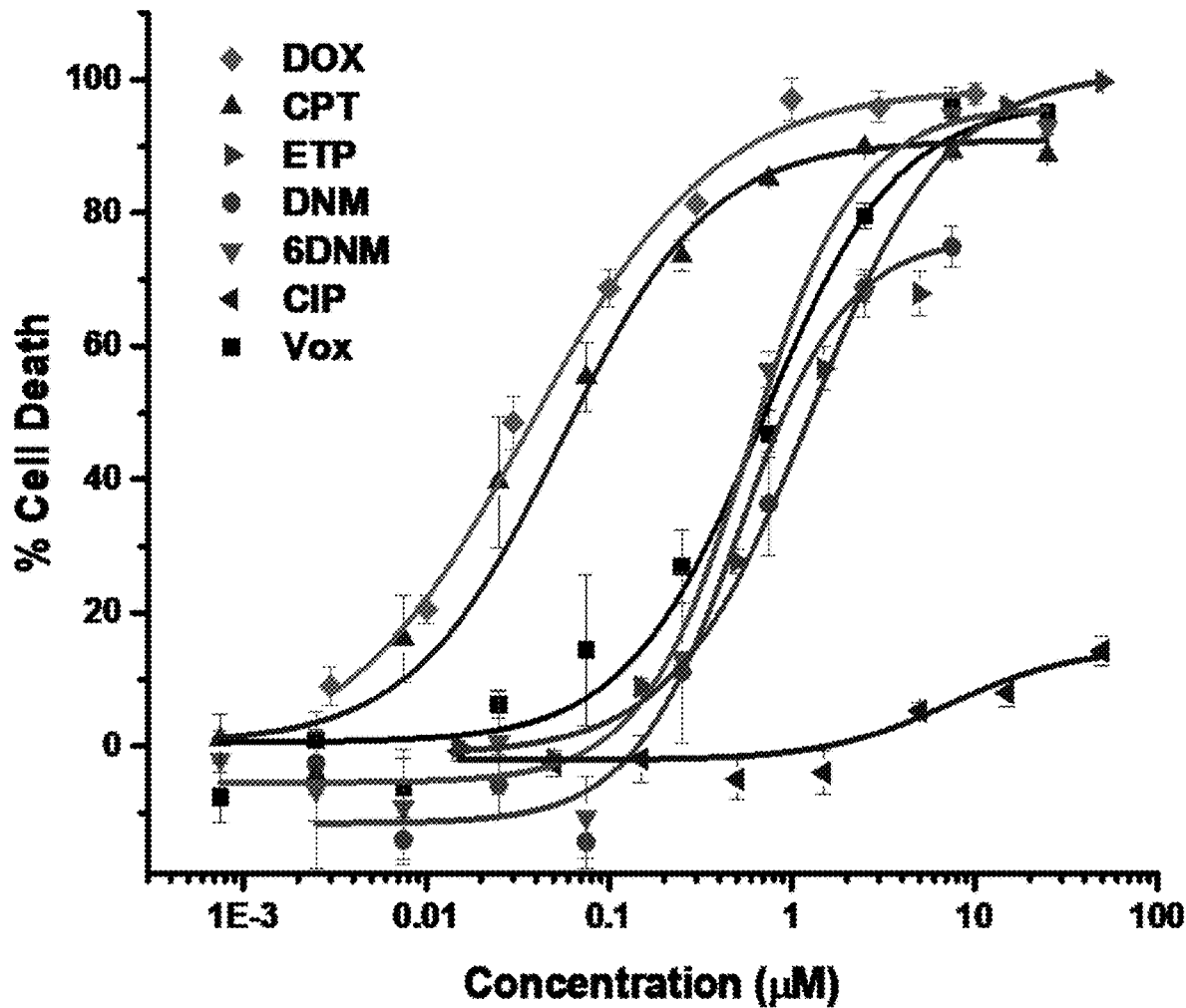
FIG. 1. DNM possesses similar antiproliferative activity compared to known topoisomerase inhibitors. Effects of DNM, 6DNM and topoisomerase inhibitors against MDA-MB-231 triple negative breast cancer cells. Cell death measured by SRB assay after 72 hour of compound exposure (n≥3 biological replicates, error bars show SEM). IC50 values given as mean±SEM from ≥3 biological replicates.
Figure 1:
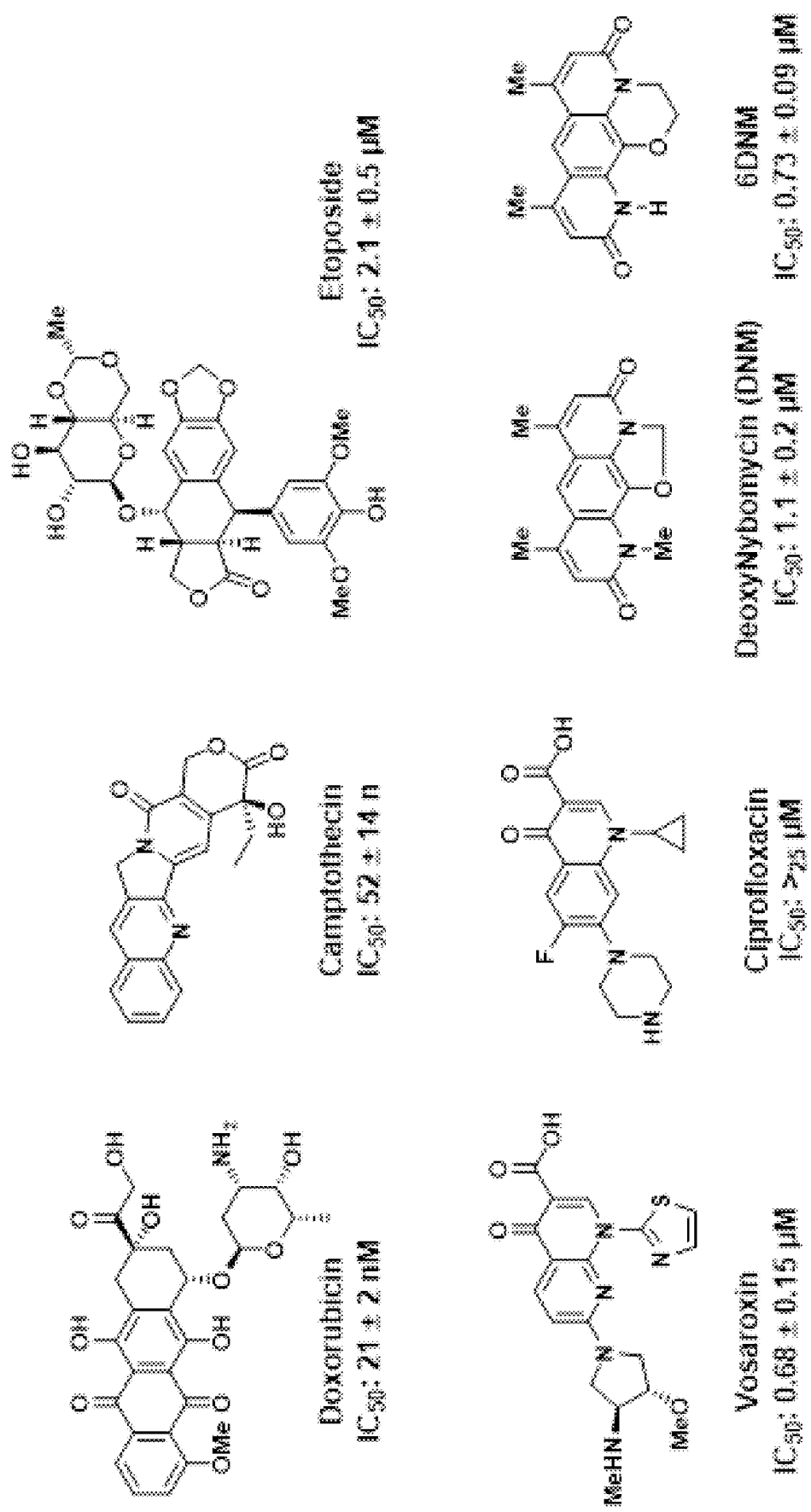

Based on the safety and in vivo effectiveness of antibiotic deoxynybomycins, which target DNA gyrase, this natural product class appears as an outstanding candidate for conversion of an antibiotic into a potent anticancer drug, or a dual action drug. In addition, such efforts would also allow a full investigation of this conversion strategy on a novel chemical scaffold.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or (C$_1$-C$_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "enantiomerically enriched" ("ee") as used herein refers to mixtures that have one enantiomer present to a greater extent than another. Reactions that provide one enantiomer present to a greater extent than another would therefore be "enantioselective" (or demonstrate "enantioselectivity"). In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%. The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

Embodiments of the Invention

This disclosure provides various embodiments of a compound of Formula I:

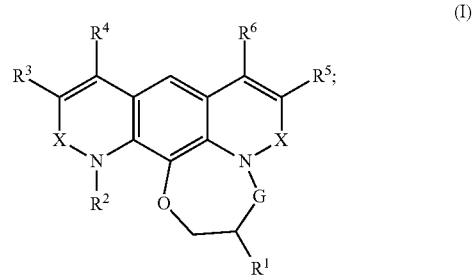

(I)

or a salt or solvate thereof;
wherein
G is a direct bond or CH$_2$;
each X is independently CH$_2$ or C=O;
R$^1$ is H, —(C$_1$-C$_6$)alkyl, —OR$^A$, —SR$^A$, —S(=O)$_2$N(R$^A$)$_2$, —N(R$^A$)$_2$, —(C$_1$-C$_5$)alkyl-OR$^A$, —(C$_1$-C$_5$)alkyl-SR$^A$, —(C$_1$-C$_5$)alkyl-S(=O)$_2$N(R$^A$)$_2$, —(C$_1$-C$_5$)—N(R$^A$)$_2$, or —(C$_1$-C$_5$)alkyl-C(=O)R$^B$;
R$^2$ is H, —(C$_1$-C$_6$)alkyl, or —(C$_3$-C$_6$)cycloalkyl;
each R$^3$ and R$^4$ are independently H, —(C$_1$-C$_6$)alkyl, or R$^3$ and R$^4$ taken together form a cycloalkyl or an aryl;
each R$^5$ and R$^6$ are independently H, —(C$_1$-C$_6$)alkyl, or R$^5$ and R$^6$ taken together form a cycloalkyl or an aryl;

R$^A$ is H, —(C$_1$-C$_6$)alkyl, —(C$_3$-C$_6$)cycloalkyl, or —C(=O)R$^B$; and

R$^B$ is H, —(C$_1$-C$_6$)alkyl, —OH, or —NH$_2$;

wherein each —(C$_1$-C$_6$)alkyl, —(C$_3$-C$_6$)cycloalkyl and aryl are optionally substituted with one or more substituents (or 1-5 substituents, or 1-2 substituents) and optionally both R$^A$ in —N(R$^A$)$_2$ taken together form a 5- or 6-membered heterocycle.

In other embodiments, R$^1$ is H, —CH$_2$OH, —CH$_2$(C=O)OH, —CH$_2$NH$_2$, —CH$_2$-(pyrrolidine), —CH$_2$-(piperidine), —CH$_2$-(piperazine), —CH$_2$-(morpholine), —CH$_2$-(imidazole), —CH$_2$-(triazole), —CH$_2$-(tetrazole). In yet other embodiments, R$^2$ is an aryl or an alkylamine, such as —(C$_1$-C$_6$)alkyl-NH$_2$. In further embodiments, the moiety —OCH$_2$CH(R$^1$)GN— in Formula I is —OCH(R$^1$)N—.

This disclosure provides additional embodiments, wherein the compound is a compound of Formula II, or Formula III:

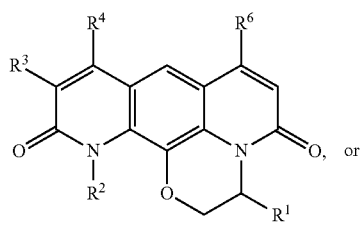
(II)

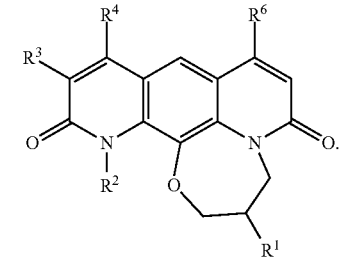
(III)

In other embodiments, R$^1$ is not H and the compound is the (R)-enantiomer or the (S)-enantiomer. In some other embodiments, R$^2$ and R$^6$ are —(C$_1$-C$_6$)alkyl. In further embodiments, R$^4$ is —(C$_1$-C$_6$)alkyl. In yet other embodiments, R$^3$ and R$^4$ taken together form a cycloalkyl or an aryl, such as a cyclopentyl, cyclohexyl or phenyl. Similarly, R$^5$ and R$^6$ taken together form a cycloalkyl or an aryl, such as a cyclopentyl, cyclohexyl or phenyl.

In various additional embodiments, the disclosed compound is a compound of Formula IV:

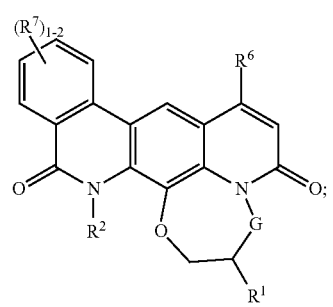
(IV)

wherein each R$^7$ is independently H, halo, —(C$_1$-C$_6$)alkyl, —OR$^A$, —SR$^A$, —N(R$^A$)$_2$, —C(=O)R$^B$, —C(=O)N(R$^A$)$_2$, or —S(=O)$_2$N(R$^A$)$_2$. There can be one or two occurrences of R$^7$ as indicated by the subscript in Formula IV.

In further embodiments, the compound is a compound of Formula V:

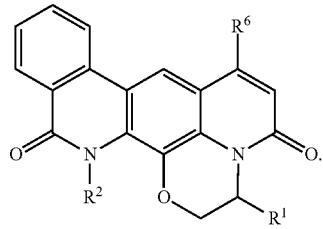
(V)

In yet other embodiments, the compound is any one of compounds C1-C20:

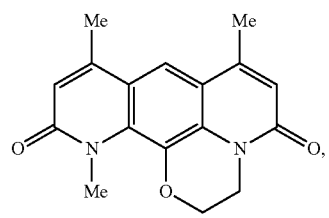
C1

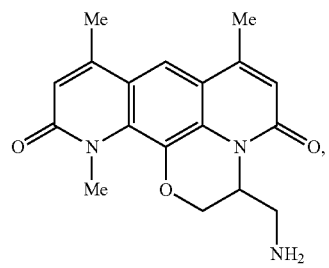
C2

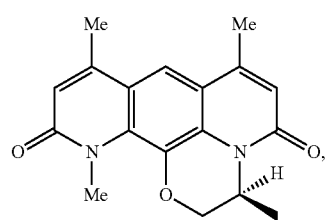
C3

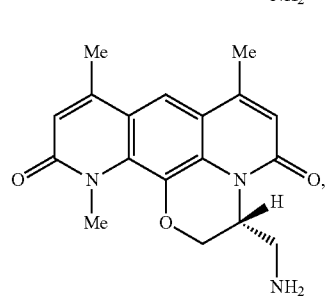
C4

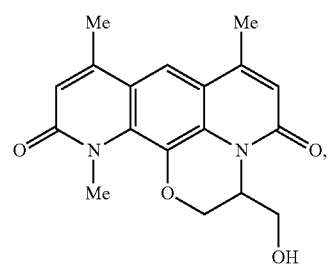
C5
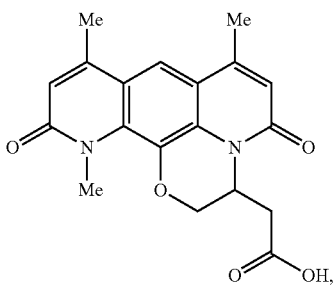
C6
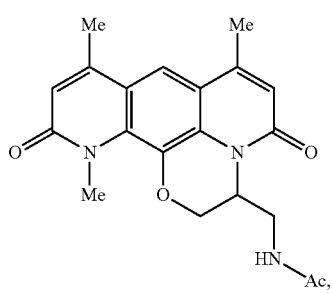
C7
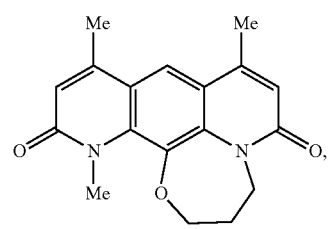
C8
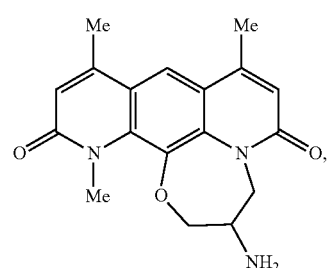
C9
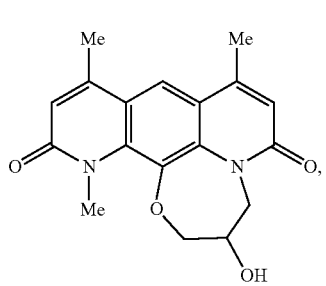
C10
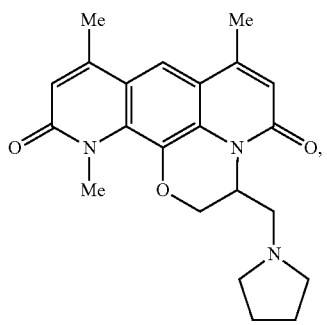
C11
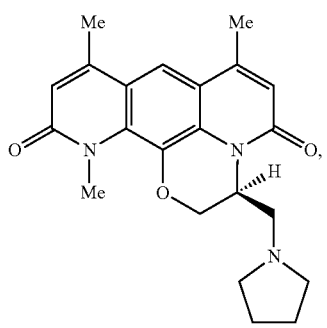
C12
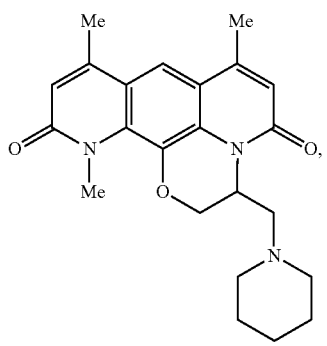
C13
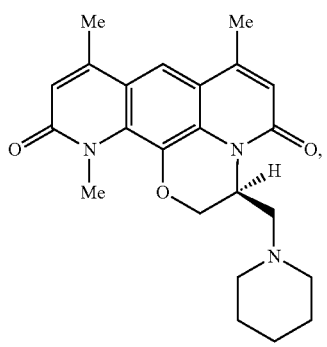
C14

C15
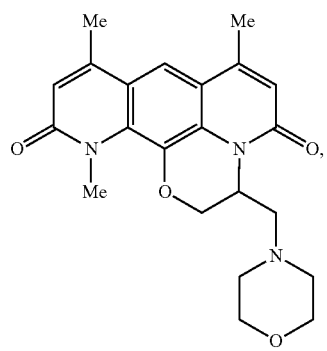
C16
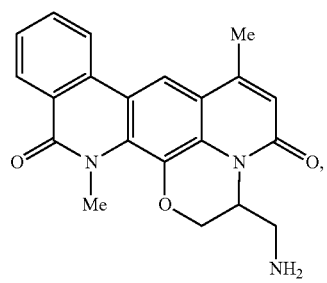
C17
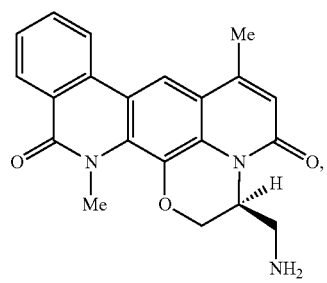
C18
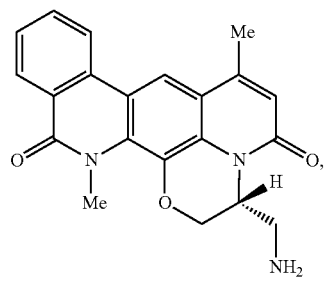
C19
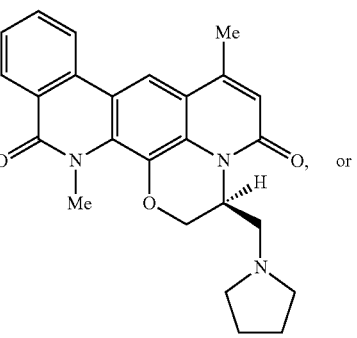
C20
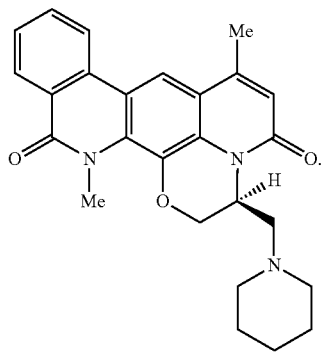
In yet further embodiments, the compound is any one of compounds C21-C28:
C21
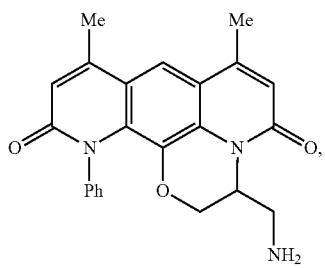
C22
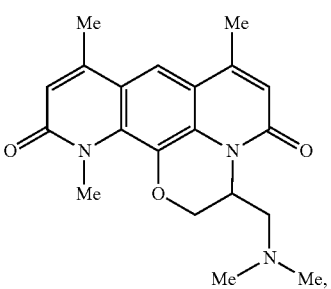
C23
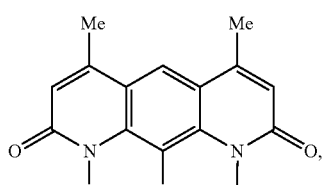
C24
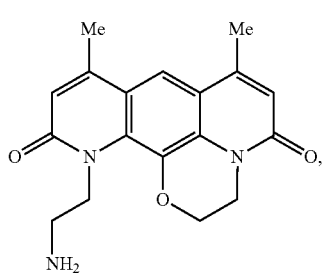

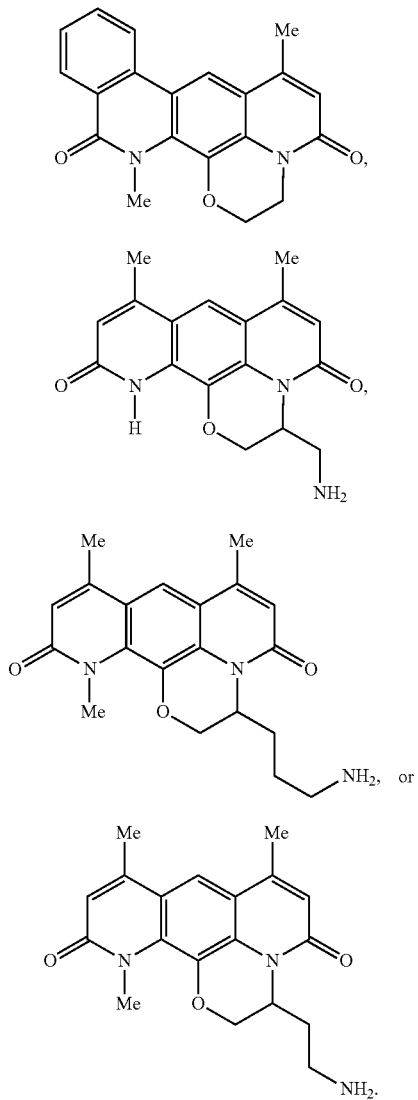

This disclosure provides additional embodiments wherein the compound inhibits topoisomerase II, or the compound inhibits bacterial growth. In other embodiments, the bacterial growth is methicillin-resistant *Staphylococcus aureus* (MRSA) growth, a vancomycin-resistant enterococci (VRE) growth, an *E. coli* growth, an *A. baumannii* growth, a *K. pneumoniae* growth, an *E. cloacae* growth, or *P. aeruginosa* growth.

In further embodiments, the compound inhibits a cancer. In yet other embodiments, the cancer is breast cancer, leukemia, cervical cancer, ovarian cancer, neuroblastoma, lung cancer, or osteosarcoma. In other various embodiments, the compound inhibits bacterial growth and a cancer.

Also, this disclosure provides a pharmaceutical composition comprising the disclosed compound in combination with a pharmaceutically acceptable diluent, carrier, excipient, or buffer.

Additionally, this disclosure provides a compound for use in the treatment of a bacterial infection in a patient in need thereof, wherein a therapeutically effective amount of the compound is administered to the patient. In various other embodiments, the bacterial infection is a gram-negative bacterial infection. In some other embodiments, the bacterial infection is methicillin-resistant *Staphylococcus aureus* (MRSA) infection, a vancomycin-resistant enterococci (VRE) infection, an *E. coli* infection, an *A. baumannii* infection, a *K. pneumoniae* infection, an *E. cloacae* infection, or *P. aeruginosa* infection.

Furthermore, this disclosure provides a compound for use in the treatment of a cancer in a patient in need thereof, wherein a therapeutically effective amount of the compound is administered to a patient. In various embodiments, the cancer is breast cancer, leukemia, cervical cancer, ovarian cancer, neuroblastoma, lung cancer, or osteosarcoma.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion

Antiproliferative Effects of DNM.

To investigate the feasibility of developing a class of antitumor antibiotics based upon the DNM scaffold, the ability of the DNM to exert an antiproliferative effect against MDA-MB-231 breast cancer cells was evaluated. As depicted in FIG. 1, these triple-negative breast cancer cells are sensitive to both DOX and ETP as well as the topoisomerase I (Top1) inhibitor camptothecin (CPT). In contrast, the antibiotic fluoroquinolone ciprofloxacin produces only minimal effects at doses as high as 50 μM, demonstrating its high selectivity for bacterial topoisomerases. In line with work on nybomycin, the natural product DNM is able to exert modest antiproliferative effects, however quantitative cell death is not produced, presumably due to limited aqueous solubility of the compound at higher doses (FIG. 1). A derivative of DNM, 6DNM (2), which possess improved aqueous solubility, not only produces quantitative cell death but is equipotent to the clinical trial compound vosoraxin (FIG. 1). These findings suggest the potential for DNM compounds to act as anticancer agents.

Identification of Potent Anticancer DNMs.

A series of DNM derivatives (1-23, Table 1) were prepared using a route previously developed and recently adapted for the synthesis of 6DNM-NH3 (9), the first nybomycin with broad-spectrum antibacterial activity. This flexible route appends vinyl or aryl iodides to a bis-borylated core through a mixed Suzuki-Miyaura coupling, which allows for an intramolecular Buchwald-Hartwig amidation to rapidly provide the nybomycin tricyclic core (24-26) (Scheme 1). Removal of the methyl ether and PMB protecting groups provides the 8-hydroxy-2-quinolones 27-29. Alkylation of the phenol and secondary amide with 1,1- and 1,2-dibromides accomplishes the synthesis of DNM derivatives 1-11 and 14-15. Additional substitutions to the secondary amides of 10 and 11 was accomplished with KOtBu or Chan-Lam couplings, respectively, to provide 12 and 13. The high flexibility of this synthetic route allowed for a systematic exploration of the effects of introducing polar functionality to the amides and the addition of a fused phenyl ring to the DNM scaffold.

TABLE 1

Structures of DNM derivatives and corresponding IC$_{50}$ values against MDA-MBD-23 1 cells Cell death measured by SRB assay after 72 hour of compound exposure (mean ± SEM, n ≥ 3 biological replicates).

| | |
|---|---|
| DNM, 1.1 ± 0.2 µM | 1 |
| 6DNM, 0.73 ± 0.09 µM | 2 |
| >10 µM | 3 |
| 8.3 ± 0.7 µM | 4 |
| 3.6 ± 0.6 µM | 5 |

TABLE 1-continued
Structures of DNM derivatives and corresponding IC$_{50}$ values against MDA-MBD-23 1 cells Cell death measured by SRB assay after 72 hour of compound exposure (mean ± SEM, n ≥ 3 biological replicates).
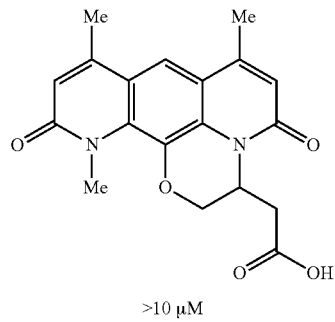 [SMILES: Cc1cc(=O)n(C)c2c3c4c(cc12)c(C)cc(=O)n4C(CC(=O)O)CO3]
6
>10 μM
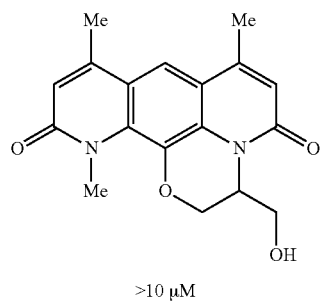 [SMILES: Cc1cc(=O)n(C)c2c3c4c(cc12)c(C)cc(=O)n4C(CO)CO3]
7
>10 μM
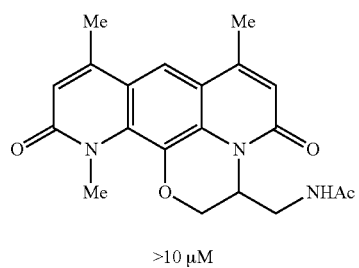 [SMILES: CC(=O)NCC1COc2c3c(cc4c(C)cc(=O)n1c24)c(C)cc(=O)n3C]
8
>10 μM
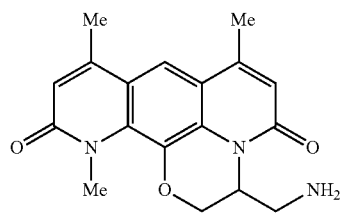
9
6DNM-NH3,
0.22 ± 0.02 μM
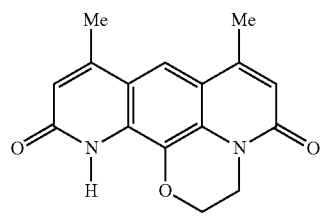
10
1.6 ± 0.2 μM TABLE 1-continued
Structures of DNM derivatives and corresponding IC$_{50}$ values against MDA-MBD-231 cells Cell death measured by SRB assay after 72 hour of compound exposure (mean ± SEM, n ≥ 3 biological replicates).
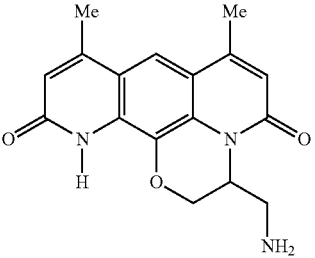
11
0.86 ± 0.07 µM
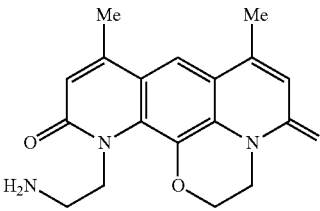
12
0.22 ± 0.06 µM
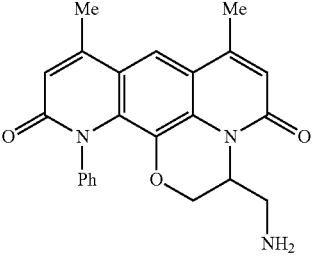
13
1.6 ± 0.6 µM
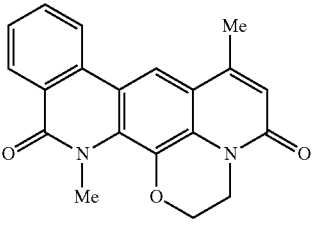
14
Ph-6DNM,
0.93 ± 0.4 µM
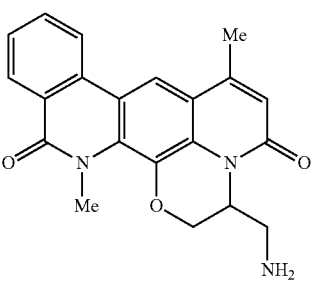
15
Ph-6DNM-NH3,
0.048 ± 0.008 µM TABLE 1-continued
Structures of DNM derivatives and corresponding IC$_{50}$ values against MDA-MBD-23 1 cells Cell death measured by SRB assay after 72 hour of compound exposure (mean ± SEM, n ≥ 3 biological replicates).
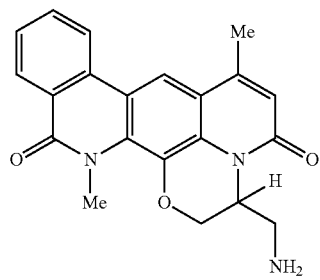
16
(S)-Ph-6DNM-NH3,
0.030 ± 0.006 µM
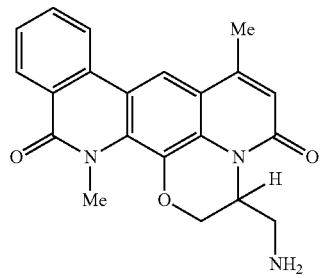
17
(R)-Ph-6DNM-NH3,
0.13 ± 0.03 µM
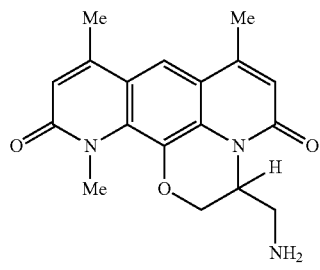
18
(S)-6DNM-NH3,
0.20 ± 0.01 µM
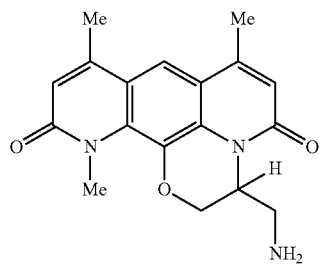
19
(R)-6DNM-NH3,
4.0 ± 0.8 µM TABLE 1-continued
Structures of DNM derivatives and corresponding $IC_{50}$ values against MDA-MBD-23 1 cells Cell death measured by SRB assay after 72 hour of compound exposure (mean ± SEM, n ≥ 3 biological replicates).
20
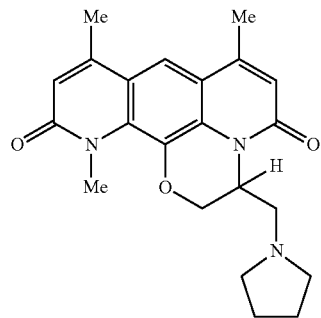
(S)-6DNM-Pyr,
0.014 ± 0.001 μM
21
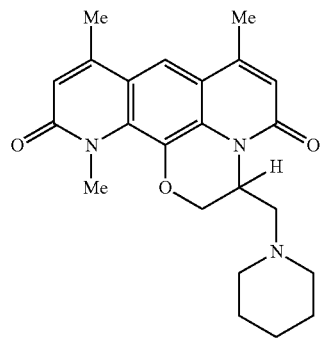
(S)-Ph-6DNM-Pip,
0.017 ± 0.001 μM
22
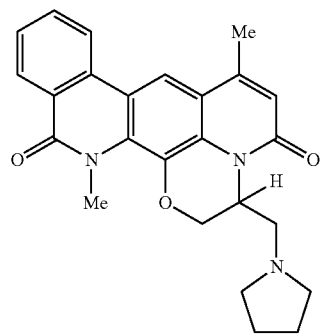
(S)-Ph-6DNM-Pyr,
0.031 ± 0.003 μM TABLE 1-continued
Structures of DNM derivatives and corresponding $IC_{50}$ values against MDA-MBD-231 cells Cell death measured by SRB assay after 72 hour of compound exposure (mean ± SEM, n ≥ 3 biological replicates).
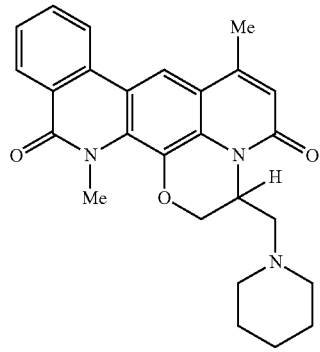
23
(S)-6DNM-Pip,
0.079 ± 0.007 µM

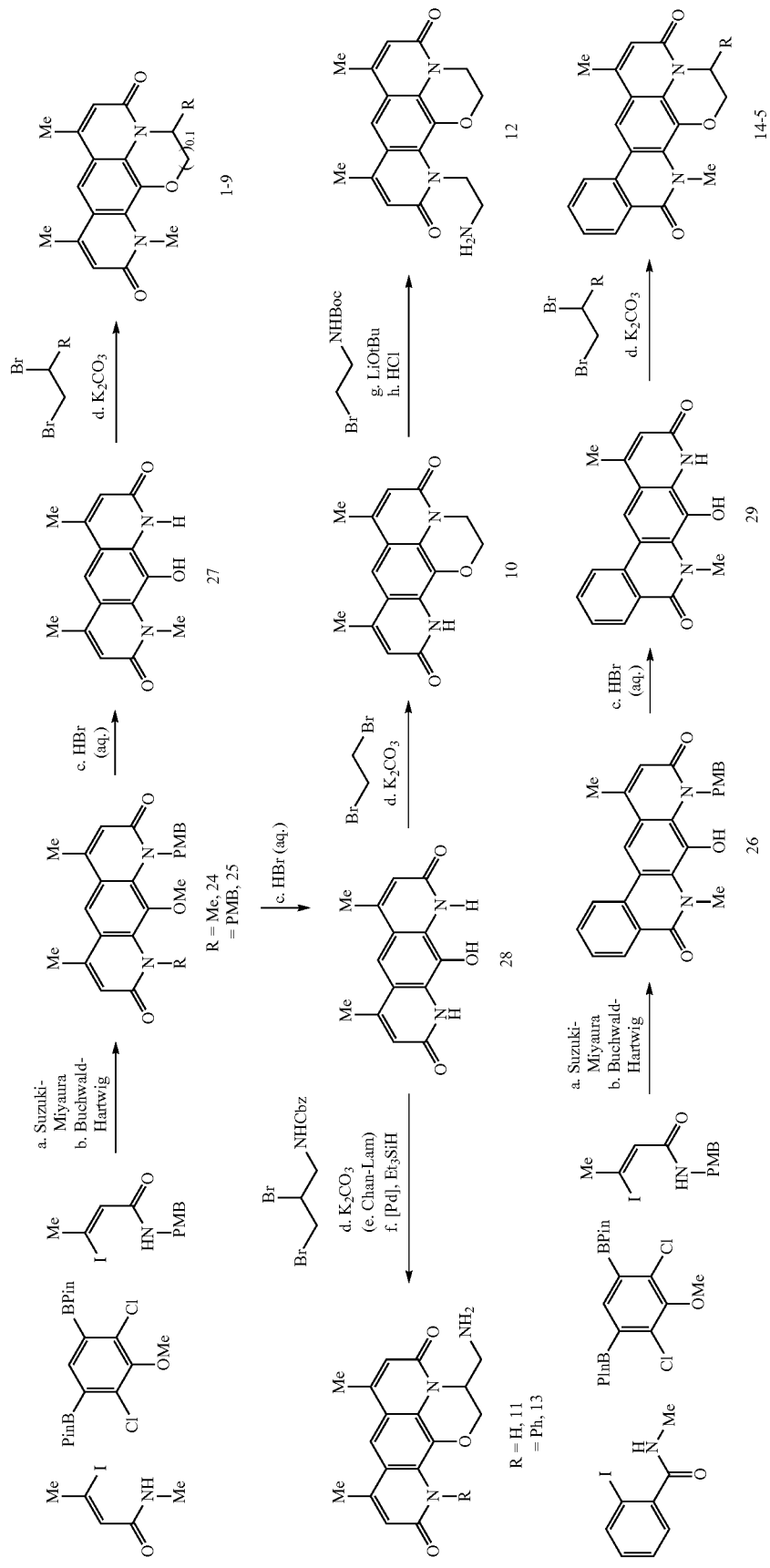
Scheme 1. Synthesis of DNM derivatives.
Reagents and Conditions. (a) PdCl$_2$(dppf)·CH$_2$Cl$_2$, K$_2$CO$_3$, DME/H$_2$O (10:1), 85° C.; (b) Pd-Xphos PreCat1, Xphos, K$_2$CO$_3$, IPA, 85° C.; (c) 48% HBr, 115° C.; (d) K$_2$CO$_3$, DMF, 85° C.; (e) Cu(OAc)$_2$, PhB(OH)$_2$, pyridine, Et$_3$N, CH$_2$Cl$_2$, (f) Pd(OAc)$_2$, Et$_3$SiH, CH$_2$Cl$_2$; (g) LiOtBu, DMF (h) HCl$_{(aq)}$ MeOH, EtOAc.

Evaluation of these novel DNM derivatives against MDA-MB-231 cells revealed several noteworthy features about the influence of the DNM scaffold on activity (Table 1). Although the addition of a carboxylic acid, ester, amide and alcohol functionality to the 5-membered ring of DNM resulted in moderate to considerable decreases in compound potency (3-8), the amine of 6DNM-NH3 produces a significant improvement in activity (compare 9 to 8 and 2). Appending an amine to the acyclic amide of 6DNM (as in 12) produces a similar increase in activity, likely due to the symmetry of DNM core. Further investigation into the substitution of this acyclic amide revealed the methyl group was optimal as either its removal (10, 11) or replacement with a phenyl ring (13) led to decreases in activity. In contrast to the minimal changes that were tolerated at the acyclic amide, the expansion of the aromatic core to produce Ph-6DNM-NH3 (15) produces a further 4.5-fold improvement in potency relative to 6DNM-NH3. This effect appears to be specific to compounds containing an amino group, as 6DNM and Ph-6DNM possess similar activity.

To investigate if the lone stereocenter might impact activity, an enantioselective synthesis of 6DNM-NH3 and Ph-6DNM-NH3 (Scheme 2) was developed. This route employs the mesylates (R)-30 and (S)-30 derived from glycidol as the dielectrophiles to provide each enantiomer (16-19) in good enantiopurity. To determine the absolute configuration of these analogues, the product of 27 and (S)-30 was crystalized from CDCl3. Single-crystal X-ray diffraction revealed the compound to be (R)-6DNM-NH3, indicating the reaction proceeds with inversion of stereochemistry, likely through an $S_N2$ mechanism. Importantly, both the (S)-enantiomers of 6DNM-NH3 and Ph-6DNM-NH3 were significantly more active than their respective (R)-enantiomers, suggesting that the compounds are not exerting their antiproliferative effects via DNA intercalation. Furthermore, DNM derivatives are only able to displace ethidium bromide from DNA at micromolar doses.

To further explore activity around the amine functionality, the primary amines of (S)-6DNM-NH3 and (S)-Ph-6DNM-NH3 were alkylated with 1,4-dibromobutane and 1,5-dibrompentane to provide the corresponding pyrollidines and piperidines (20-23) (Scheme 2). In the case of 6DNM-NH3, this substitution results in a greater than 10-fold increase in potency (Table 1). Although this drastic improvement to activity was not observed for the derivatives bearing the extended aromatic core, the hydrophobic rings were well-tolerated, with Ph-6DNM-Pyr and Ph-6DNM-Pip maintaining much of the activity of Ph-6DNM-NH3.

Scheme 2. Enantioselective synthesis of 6DNM—NH3, Ph—6DNM—NH3, and their cyclic amine derivatives.

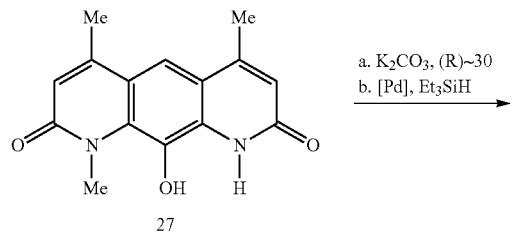

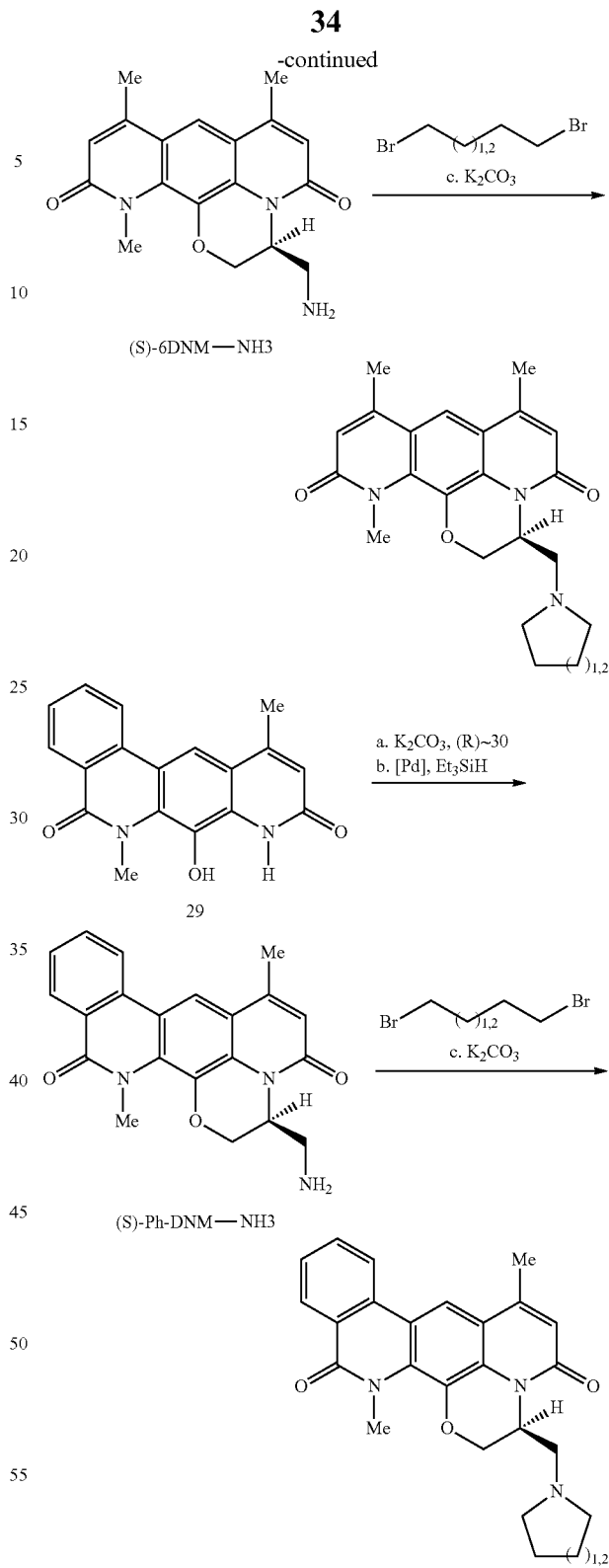

Reagents and Conditions. (a) K2CO3, DMF, 85° C.; (b) Pd(OAc)2, Et3N. Et3SiH, CH2Cl2; (c) K2CO3, MeCN, 85° C.

Figure 2:
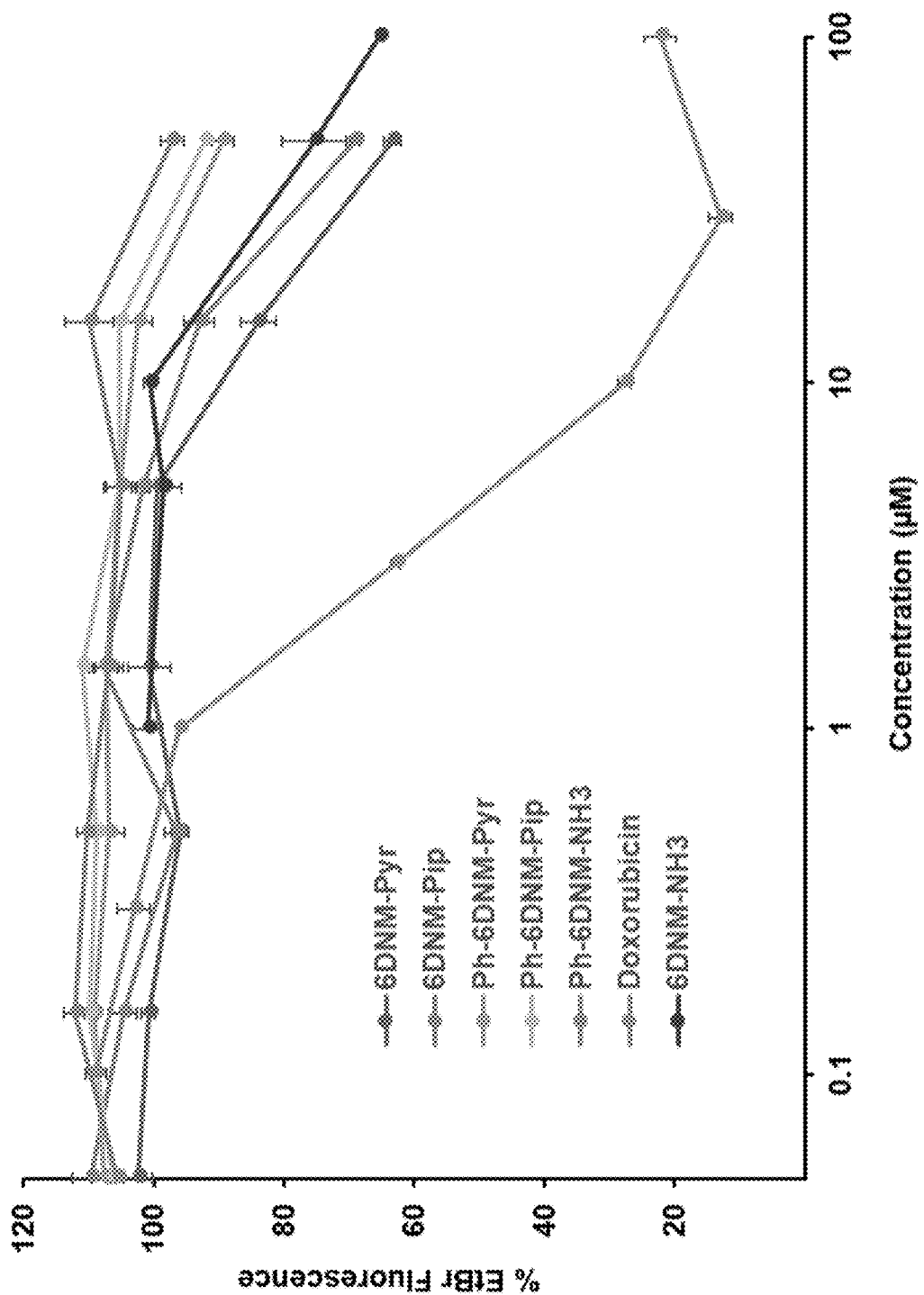
FIG. 2. DNM derivatives do not displace EtBr from herring sperm DNA. Compounds were incubated in buffer (pH=7.55) containing Herring Sperm DNA (34 µg/mL) and EtBr (5 µM) for 30 minutes at 37° C. Fluorescence was measured (excitation 545 nm, emission=595 nm) and normalized to DMSO (100%) and wells lacking DNA (0%). Data is an average of two independent experiments.

Through this systematic investigation of the anticancer activity of compounds possessing the DNM scaffold numerous derivatives were identified that have both increased and decreased ability to effect breast cancer cell growth relative to the natural product DNM. Because nybomycins are also known to possess considerable antibacterial effects, these less active derivatives may represent compounds with high selectivity for bacterial topoisomerases. To investigate this possibility, the antibacterial effects of the DNM derivatives was assessed against strains of *E. coli, S. aureus*, and MRSA using the microbroth dilution method (Table 2). In general, similar trends for the anticancer effects were observed for their antibacterial effects against both Gram-negative and Gram-positive wild-type bacteria (FIG. 2). However, 3 and 7, which possesses reduced activity in cancer cells remains effective against MRSA indicating their promising potential as antibacterial compounds.

TABLE 2

Antibacterial activity of DNM derivatives.

| Compound | MDA-MB-231 IC$_{50}$ (μM) | E. coli MIC (μg/mL) | S. aureus MIC (μg/mL) | MRSA MIC (μg/mL) |
| --- | --- | --- | --- | --- |
| 1 | 1.1 ± 0.2 | >16 | 2 | 0.03 |
| 2 | 0.73 ± 0.09 | >16 | 1 | 0.06 |
| 3 | >10 | >16 | >16 | 0.5 |
| 4 | 8.3 ± 0.7 | >16 | >16 | 4 |
| 5 | 3.6 ± 0.6 | >32 | >32 | 2 |
| 6 | >10 | >32 | >16 | 16 |
| 7 | >10 | >16 | 16 | 0.25 |
| 8 | >10 | >16 | 32 | 0.5 |
| 9 | 0.22 ± 0.02 | 0.5 | 0.5 | 0.03 |
| 10 | 1.6 ± 0.2 | >32 | 4 | — |
| 11 | 0.86 ± 0.07 | 2 | 4 | — |
| 12 | 0.22 ± 0.06 | 4 | 4 | — |
| 13 | 1.6 ± 0.6 | >16 | >16 | — |
| 14 | 0.93 ± 0.4 | >16 | 2 | 0.5 |
| 15 | 0.048 ± 0.008 | 0.25 | 1 | 1 |
| 16 | 0.030 ± 0.006 | 0.25 | 1 | — |
| 17 | 0.13 ± 0.03 | 2 | 4 | — |
| 18 | 0.20 ± 0.01 | 0.25 | 0.5 | — |
| 19 | 4.0 ± 0.8 | >16 | 32 | — |
| 20 | 0.014 ± 0.001 | 1 | 0.5 | — |
| 21 | 0.017 ± 0.001 | 4 | 0.5 | — |
| 22 | 0.031 ± 0.003 | 1 | 0.25 | — |
| 23 | 0.079 ± 0.007 | 2 | 0.5 | — |

Activity Against Panel of Cancer Cell Lines.

Topoisomerase inhibitors such as DOX are used as single agent and in combination therapy to treat a wide-range of cancer types. To determine if this same broad applicability would also apply to the DNM class of antitumor antibiotics, the most potent derivatives were selected and evaluated against a panel of 10 cancer cell lines representative of the tissue types commonly treated with doxorubicin, including breast, colon, ovarian, cervical, lung, bone, blood, and nerve. As depicted in Table 3, these derivatives possess potent activity against the cell lines of this panel with mean IC$_{50}$ values ranging from 25-164 nM, values comparable to that found for doxorubicin (55 nM). In general, the differences in sensitivities of the cells to the DNM analogues mirror that of doxorubicin, however there are several notable exceptions. Primarily, the leukemia cell lines, HL-60 and Jurkat, were considerable less sensitive to Ph-6DNM-NH3 and Ph-6DNM-Pip. Similarly, these two derivatives were less effective against the ER-positive breast cancer cell line BT474, as was doxorubicin. These subtle differences in cell line specificity potentially suggest a difference in the mechanism of action for these structurally-related compounds. In order to investigate this possibility, studies aimed at elucidating the mechanism of action of 6DNM-NH3, Ph-6DNM-NH3 and 6DNM-Pyr were conducted.

TABLE 3

Antiproliferative effects of potent anticancer DNM derivative against a panel of cancer cells.[a]

| Cell Line | Ph-6DNM-NH3 | Ph-6DNM-Pyr | Ph-6DNM-Pip | 6DNM-Pyr | 6DNM-Pip | Doxorubicin |
| --- | --- | --- | --- | --- | --- | --- |
| MDA-MB-231[c] | 30 ± 6 | 31 ± 3 | 79 ± 7 | 14 ± 1 | 17 ± 1 | 21 ± 2 |
| BT-474[c] | 690 ± 50 | 235 ± 1 | 1000 ± 100 | 91 ± 4 | 90 ± 10 | 260 ± 70 |
| HCT-116[d] | 37 ± 13 | 23 ± 3 | 79 ± 10 | 9 ± 1 | 8 ± 1 | — |
| HeLa[e] | 56 ± 5 | 46 ± 2 | 136 ± 5 | 27 ± 1 | 46 ± 2 | 24 ± 9 |
| ES-2[f] | 28 ± 6 | 23 ± 4 | 67 ± 8 | 17 ± 4 | 22 ± 6 | 32 ± 3 |
| IMR32[g] | 8.6 ± 0.1 | 4.9 ± 0.1 | 20 ± 0.2 | 4.4 ± 0.3 | 6.0 ± 1.6 | 2.9 ± 0.4 |
| H460[h] | 12 ± 2 | 7.2 ± 0.6 | 24 ± 2 | 6.6 ± 0.5 | 11 ± 2 | 6.1 ± 1 |
| HOS[i] | 17 ± 1 | 16 ± 0.4 | 55 ± 1 | 16 ± 2 | 21 ± 3 | 19 ± 7 |
| Jurkat[b,j] | 290 ± 30 | 69 ± 7 | 240 ± 40 | 20 ± 6 | 33 ± 4 | 17 ± 3 |
| HL-60[b,j] | 470 ± 90 | 94 ± 6 | 440 ± 130 | 48 ± 11 | 55 ± 11 | 84 ± 11 |
| Average | 164 | 55 | 214 | 25 | 31 | 55 |

[a]Values represent 72 hour IC$_{50}$ (nM, mean ± SEM) as measured by SRB assay unless otherwise noted.
[b]Cell viability measured using Alamar Blue assay.
[c]Breast cancer.
[d]Colon cancer.
[e]Ovarian cancer.
[f]Cervical cancer.
[g]Neuroblastoma.
[h]Lung cancer.
[i]Osteosarcoma.
[j]Leukemia.

Mechanism of Action.

DNM and its derivatives exert their antibacterial effects through inhibition of the DNA Gyrase. Similarly, 6DNM-NH3 and Ph-6DNM-NH3, are able to inhibit purified E. coli DNA Gyrase and TopoIV in supercoiling and decatenation assays, respectively. Furthermore, a spontaneous resistant mutant of E. coli MG1655 isolated from LB agar impregnated with 6DNM-NH3 (4 µg/mL, 8×MIC) possessed a single D82N mutation in DNA Gyrase.

Figure 3:
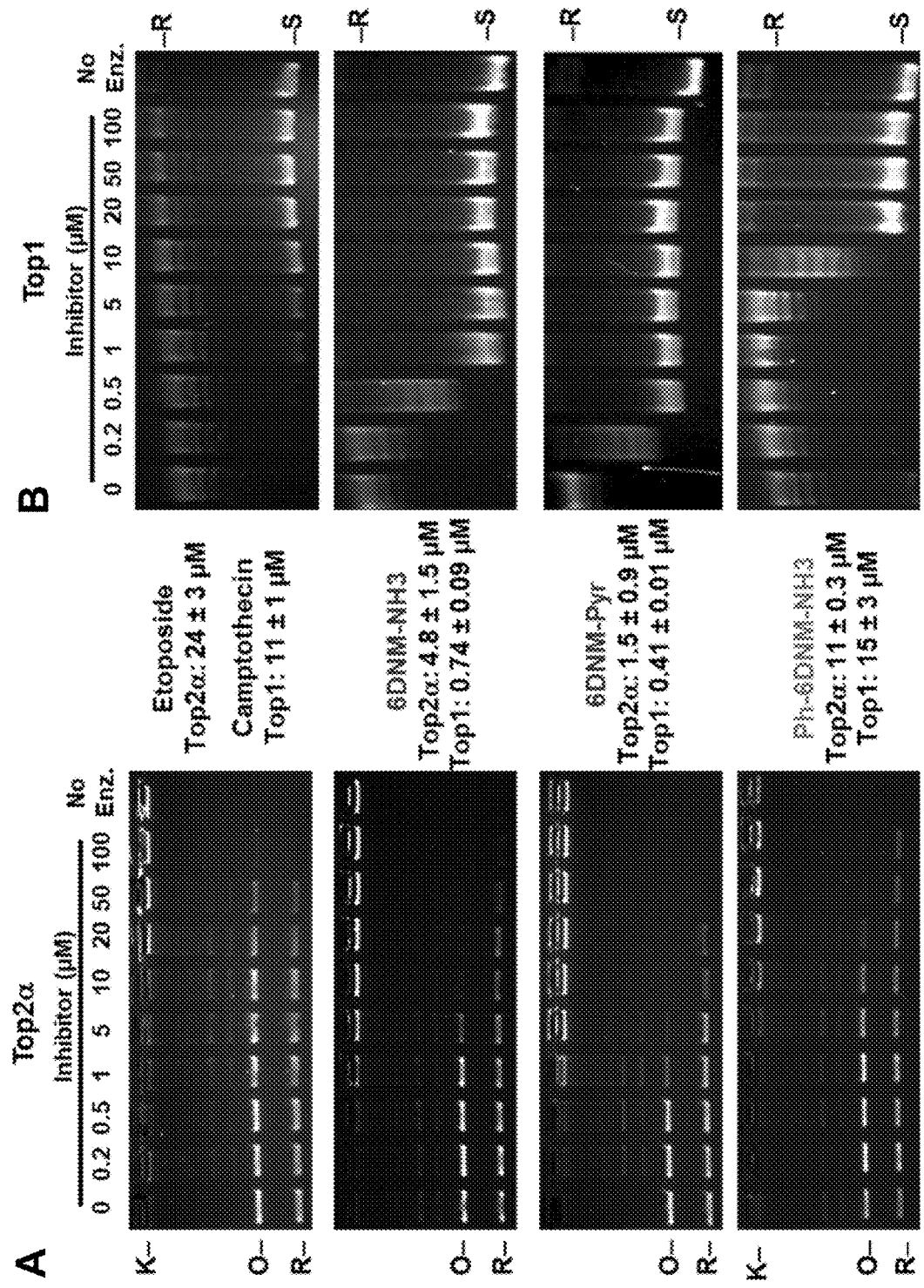
FIG. 3. DNM derivatives are dual Top1/Top2 inhibitors with different modes of inhibition. (a) Inhibition of decatenating ability of Top2α with increasing concentrations of ETP, 6DNM-NH3, 6DNM-Pyr, and Ph-6DNM-NH3. K, kinetoplast DNA; OC, open circular; R, relaxed. (b) Inhibition of relaxing ability of Top1 with increasing concentrations of CPT, 6DNM-NH3, 6DNM-Pyr, and Ph-6DNM-NH3. R, relaxed; S, supercoiled. (c) Detection of Top2a-DNA using the ICE Assay. Genomic DNA (10 Gg) of H460 cells treated with drugs (50 µM, 30 min) was applied to nitrocellulose membrane and immunoblotted for Top2a. (d) Detection of Top1-DNA adducts using ICE Assay. Same procedure as (c) using 1 µg of DNA. (e) Inhibition of ETP-induced poisoning of Top2a. H460 cells treated with indicated concentrations of inhibitor for 30 min prior to treatment with ETP (50 µM). Detection of Top2α as in (c).
Figure 3:
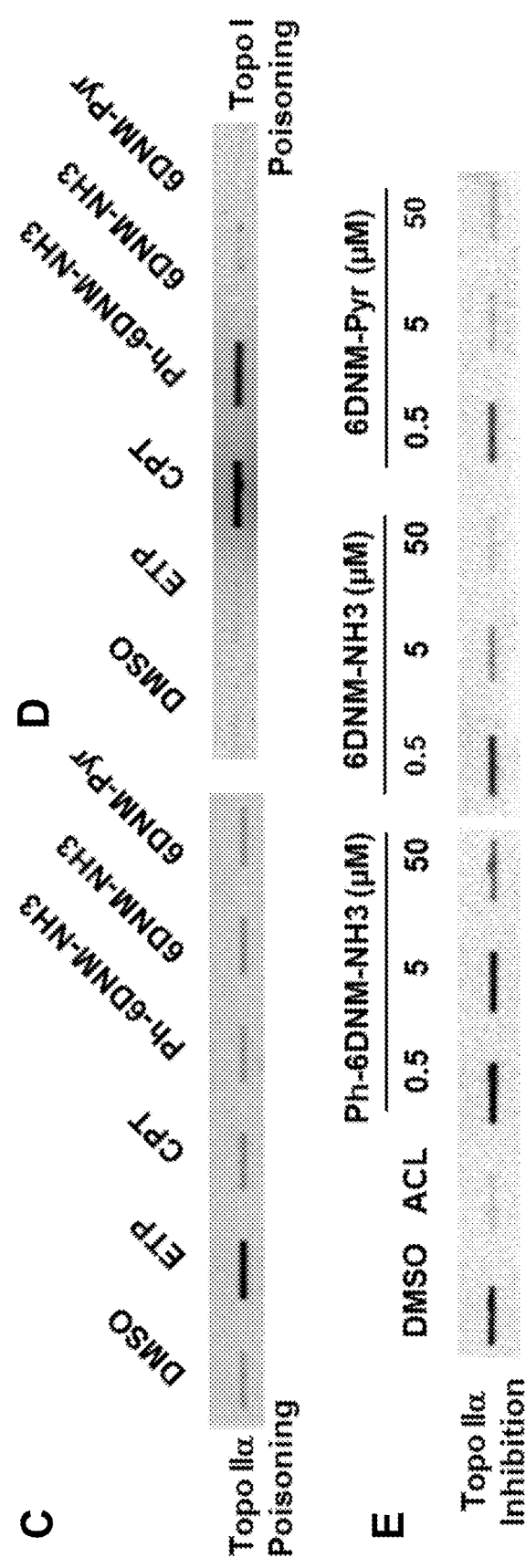
Figure 6:
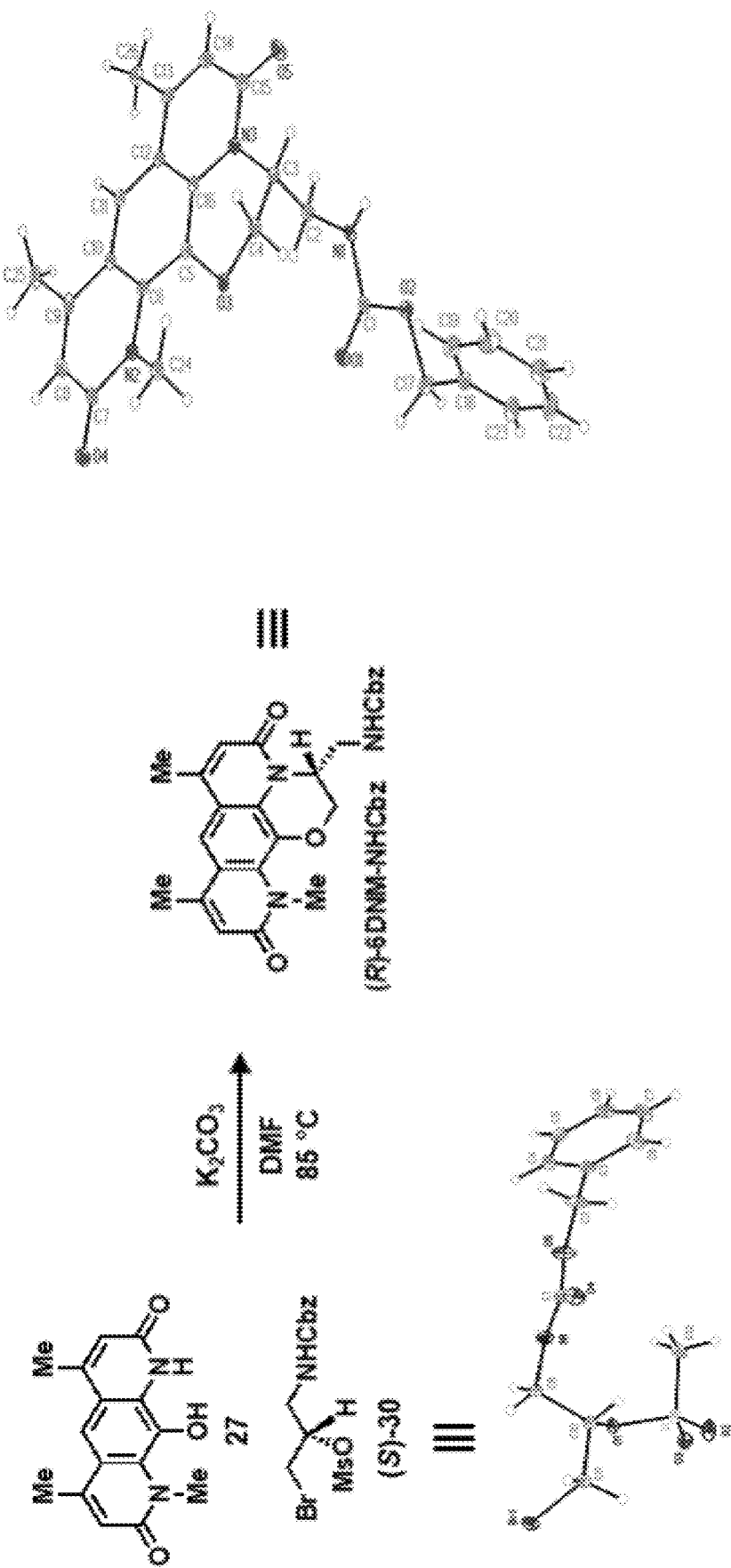
FIG. 6. Single crystal X-ray diffraction confirms the inversion of the stereogenic center within (S)-30 to produce (R)-6DNM-NHCbz.
Figure 7:
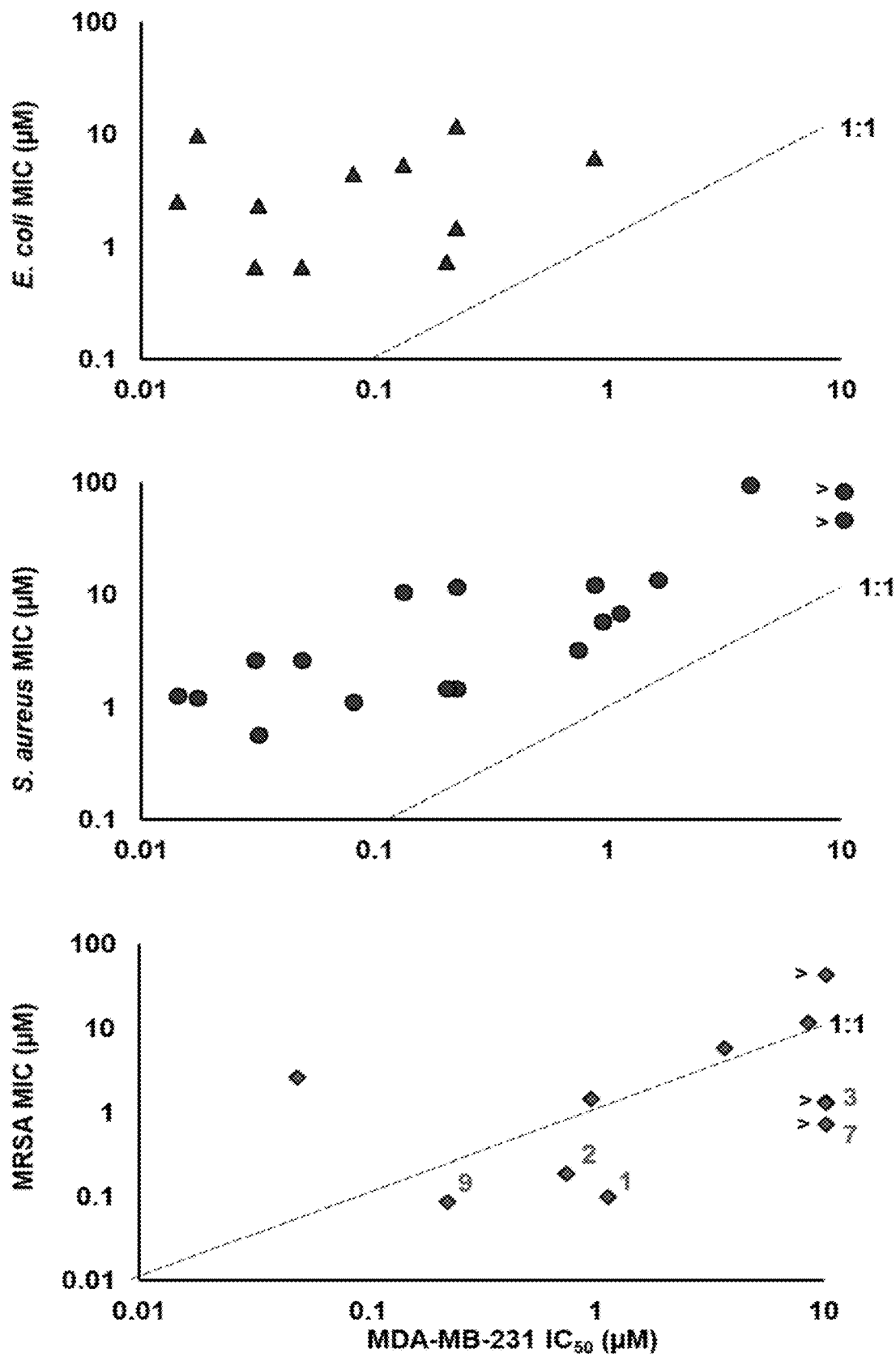
FIG. 7. Comparisons of the cytotoxicity of DNM derivatives in cancer cells to their antibacterial activities against E. coli, wild-type S. aureus, and FQR MRSA. Compounds with MIC>16 µg/mL omitted for clarity. Data points marked with ">" indicate compounds with $IC_{50}$'s greater than 1 µM. Compound numbers indicated for compounds with MIC<$IC_{50}$.
Figure 8:
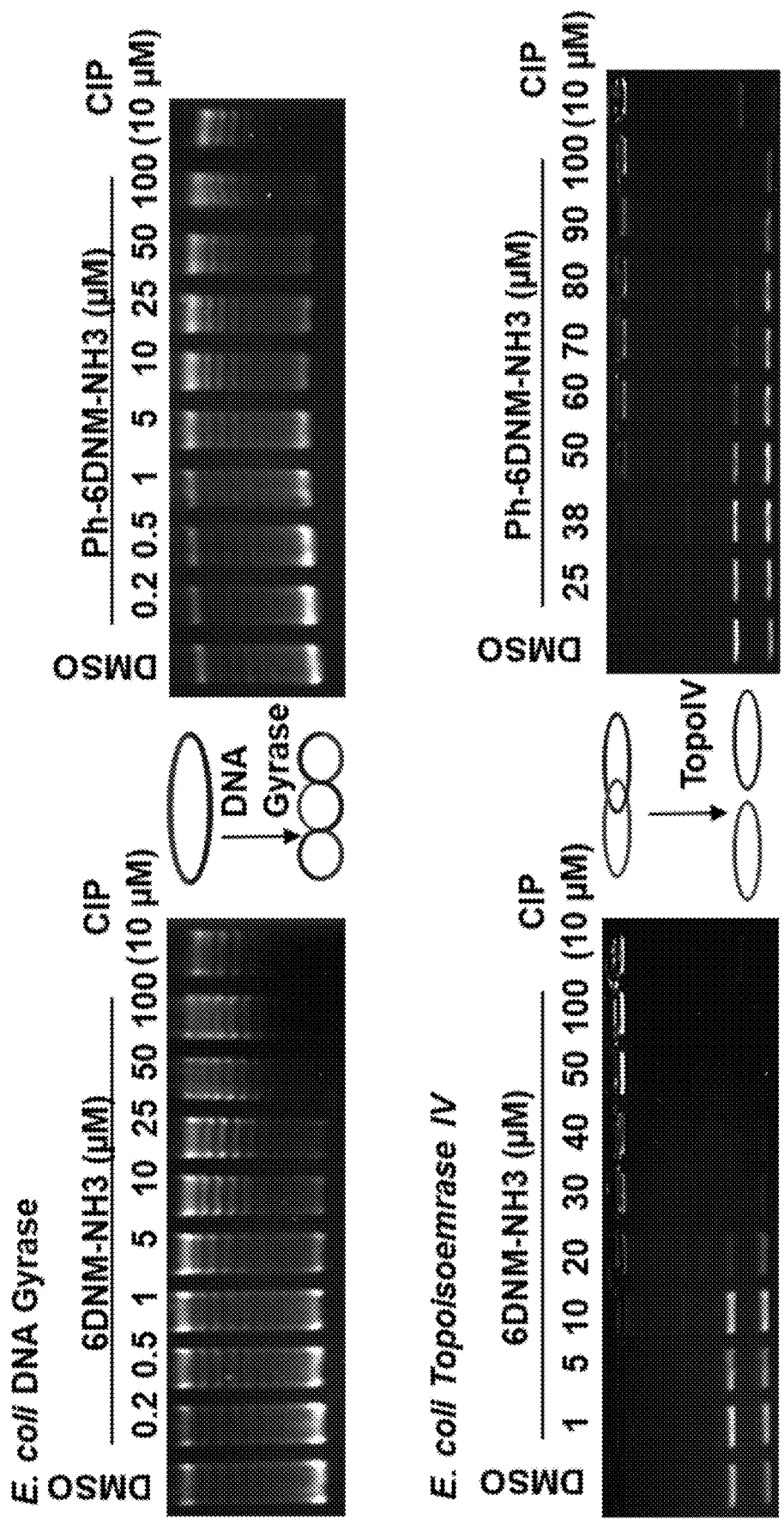
FIG. 8. In vitro inhibitory activity of 6DNM-NH3, Ph-6DNM-NH3 against E. coli DNA gyrase and TopoIV.
Figure 9:
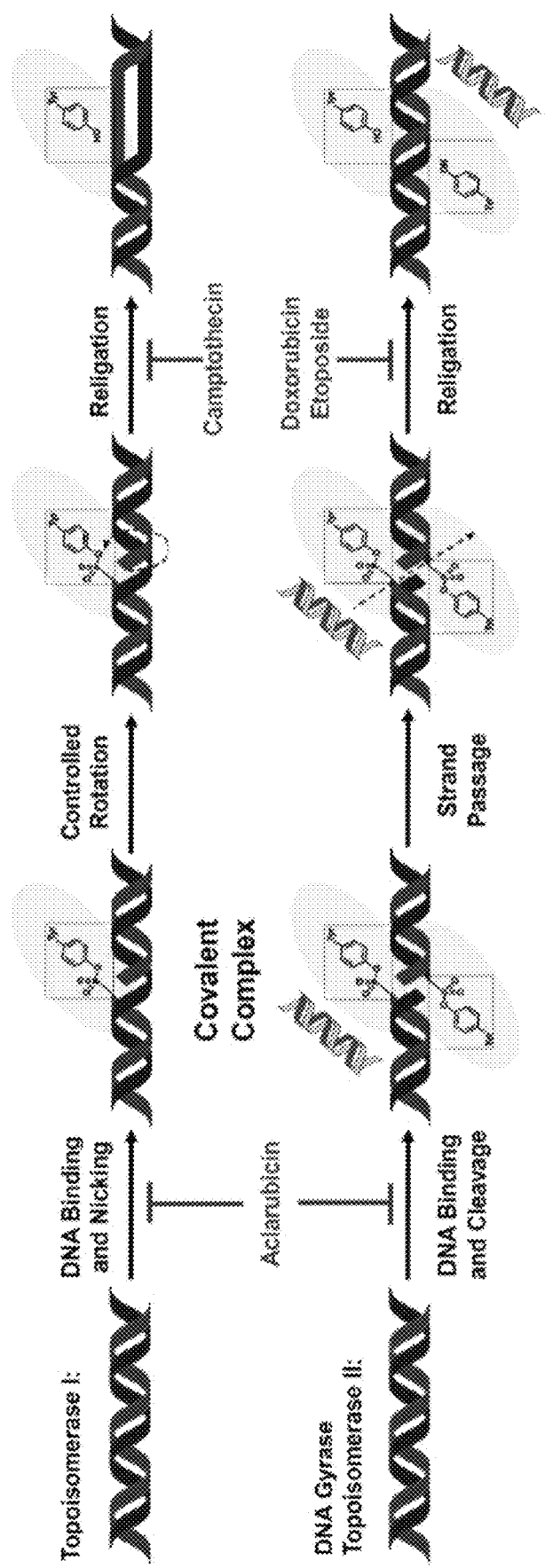
FIG. 9. Mechanism of action studies: Topoisomerases form transient covalent complexes with DNA to modify DNA topology. Ph6DNM-NH3 and 6DNM-NH3 inhibit bacterial DNA gyrase and human topoisomerase II in vitro.

The ability of Ph-6DNM-NH3, 6DNM-NH3, and 6DNM-Pyr to inhibit Top2α was assessed using a decatenation assay. In this assay, Top2α is incubated with kinetoplast DNA (kDNA), a large network of catenated minicircles and maxicircles of DNA. As Top2α decatenates the kDNA, it releases supercoiled and relaxed DNA minicircles that are easily separated from the kDNA by gel electrophoresis. All three DNM derivatives inhibit the decatenating function of Top2α in a dose-dependent manner and are more potent than the clinically-used topoisomerase inhibitor etoposide (FIG. 3a). The relatively potency of 6DNM-Pyr and 6DNM-NH3 corroborates the results observed in cell culture, with 6DNM-Pyr inhibiting Top2α function at lower concentrations than 6DNM-NH3. Intriguingly, Ph-6DNM-NH3, which in most cell lines is as effective as 6DNM-Pyr and more effective than 6DNM-NH3, is the least active derivative in this in vitro assay.

To further investigate any mechanistic differences between these structurally related DNM analogues they were also evaluated against the other clinically-targeted mammalian topoisomerase, Top1, using a DNA relaxation assay in which purified Top1 relaxes supercoiled pBR322 and the two forms are separated by agarose gel electrophoresis. As depicted in FIG. 3b, both 6DNM-NH3 and 6DNM-Pyr are potent inhibitors of Top1 able to inhibit relaxation at submicromolar concentrations. By comparison, Ph-6DNM-NH3 is more than 20-fold less potent of an inhibitor than 6DNM-Pyr and approximately equipotent to the known Top1 inhibitor camptothecin (CPT).

Next explored was whether the apparent differences between in vitro topoisomerase inhibition and the effects in cell culture might be rationalized by the mode of inhibition.

Topoisomerase inhibitors used in cancer chemotherapy—including DOX, ETP, and CPT derivatives—act by stabilizing so-called cleavage complexes (Top1cc and Top2cc) formed as the topoisomerases form covalent adducts between active-site tyrosines and the phosphate backbone of DNA. This trapping of the topoisomerases leads to DNA damage ultimately resulting in apoptotic cell death. As such, topoisomerases that stabilize Top1cc and Top2cc are referred to as topoisomerase poisons. Compounds that do not operate through this poisoning mechanism but are capable of inhibiting the catalytic function of topoisomerases are referred to as catalytic inhibitors.

The in vivo complex of enzyme (ICE) assay can be used to distinguish poisons from catalytic inhibitors. The ICE assay consists of isolating the genomic DNA of cells treated with small molecules in a manner the preserves covalent DNA-protein complexes and applying it to nitrocellulose membranes. Because topoisomerase poisons stabilize the cleavage complexes, DNA-protein complexes can be detected by immunoblotting for specific topoisomerases, whereas catalytic inhibitors produce no such result. To determine if DNM derivatives are acting as poisons or catalytic inhibitors, H460 human lung cells were exposed to 50 µM of the Top2 poison ETP, Ph-6DNM-NH3, 6DNM-NH3, and 6DNM-Pyr and assessed for their ability to stabilize Top2cc. As seen in FIG. 3a, only ETP treatment resulted in the accumulation of Top2cc. However, pretreatment with the DNM derivatives 30-minutes prior to ETP treatment led to a dose-dependent decrease in ETP-induced Top2cc (FIG. 3c) indicating that these DNM derivatives are catalytic inhibitors of Top2α. Furthermore, the degree of inhibition is an agreement with the results from in vitro assay, with 6DNM-Pyr being considerably more effective than Ph-6DNM-NH3 at inhibiting ETP-induced Top2cc. In a similar fashion, next investigated was the mode of Top1 inhibition using the ICE assay (FIG. 3b). Surprisingly, treatment with Ph-6DNM-NH3, but neither 6DNM-NH3 nor 6DNM-Pyr, leads to the accumulation of Top1cc (FIG. 3c). Taken together, results from in vitro and cell culture experiments indicate that 6DNM-NH3 and 6DNM-Pyr act as dual Top1/Top2α catalytic inhibitors, whereas Ph-6DNM-NH3 is a Top1 poison/Top2α catalytic inhibitor (FIG. 3e).

This difference in mechanism of action between Ph-6DNM-NH3 and 6DNM-Pyr may provide an explanation of the differences in cell line sensitivities between the different DNM derivatives. Previous studies have demonstrated that certain cell lines are able to degrade Top1 via the proteasome in response to treatment with CPT. This downregulation serves as a resistance mechanism and the level of Top1 degradation is correlated with reduced sensitivity to CPT. To determine if a similar mechanism is responsible for the reduced sensitivity to Ph-6DNM-NH3 and its derivatives in certain cell lines, the effects of Ph-6DNM-NH3 and 6DNM-Pyr were compared to that of CPT in HCT-116 and BT-474, two cancer cell lines known to be deficient and proficient in Top1 degradation, respectively. Cells were treated with 50 µM Ph-6DNM-NH3, 6DNM-Pyr, or CPT for 2, 4, and 6 hours. Following a 30-minute incubation with drug-free media to allow for the reversal of any Top1cc formed, cells were lysed and Top1 concentrations assessed by Western blot (FIG. 4a). In MDA-MB-231 cells, which is sensitive to all three compounds, minimal differences in Top1 relative to untreated cells is observed. However, in BT-474, a time-dependent decrease in the levels of Top1 is seen in Ph-6DNM-NH3 and CPT-treated cells, but minimal effect to 6DNM-Pyr-treated cells. This degradation of Top1 produces nearly complete resistance to CPT (FIG. 4b). The effectiveness Ph-6DNM-NH3 is similarly reduced, however to a lesser extent, possibly due to the ability of Ph-6DNM-NH3 to inhibit Top2.

General Synthetic Methods

This disclosure relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5$^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, N.Y., 1994), and references cited therein); and Comprehensive Organic Transformations, Larock, R. C., Second Edition, John Wiley & Sons, New York (1999), and referenced cited therein.

A number of exemplary methods for the preparation of the compounds of the invention are provided in the Examples. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. Typically, the temperatures will be $-100°$ C. to $200°$ C., solvents will be aprotic or protic depending on the conditions required, and reaction times will be 1 minute to 10 days.

Work-up typically consists of quenching any unreacted reagents followed by partition between a water/organic layer system (extraction) and separation of the layer containing the product.

Oxidation and reduction reactions are typically carried out at temperatures near room temperature (about $20°$ C.), although for metal hydride reductions frequently the temperature is reduced to $0°$ C. to $-100°$ C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures ($0°$ C. to $-100°$ C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. In addition, ability of a compound to treat cancer may be determined using standard assays known to those of skill in the art.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Compound Synthesis and Characterization

General Methods:

All reactions were performed in flame- or oven-dried glassware under an atmosphere of nitrogen unless otherwise stated. Chemical reagents were purchased from commercial suppliers and used without further purifications. Anhydrous solvents were obtained by passing through columns of alumina under nitrogen using a solvent purifications system. $^1$H spectra were recorded on Varian Unity 400 or 500 and Bruker 500 equipped with a CryoProbe at 500 MHz. $^{13}$C spectra were recorded on a Bruker 500 equipped with a CryoProbe at 125 MHz. Chemical shifts are reported in parts per million (ppm). Spectra obtained in CDCl$_3$ were referenced to the residual solvent peaks at 7.26 ppm ($^1$H NMR) and 77.16 ppm ($^{13}$C NMR). Spectra obtained in 1:1 MeOD/CDCl$_3$ were referenced to the residual methanol signal at 3.31 ppm ($^1$H NMR) and 49.00 ($^{13}$C). $^1$H NMR multiplicities are reported as: s=singlet, br=broad, d=doublet, t=triplet, q=quartet, m=multiplet. All compounds tested in biological assays were ≥95% as assessed by $^1$H NMR. High-resolution mass spectroscopy was performed on a Waters Q-TOF Ultima by the University of Illinois Mass Spectrometry Center.

Compounds 1, 2, 6, 8, 9, 24, 25, 27, 28 were prepared according to known procedures.

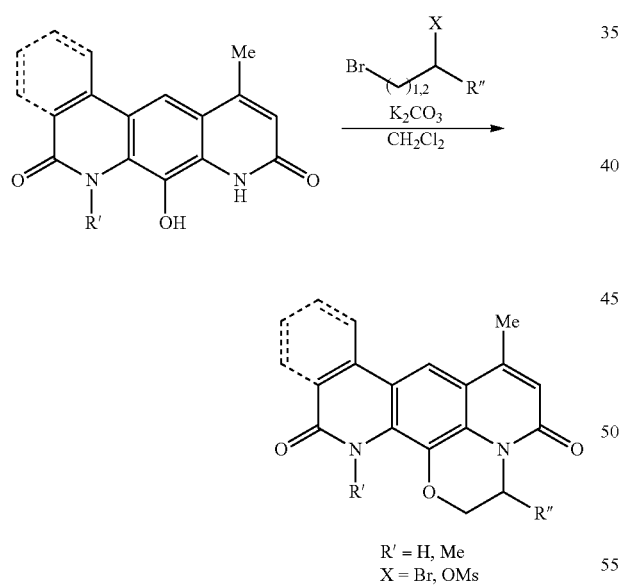

General Procedure A:

A suspension of 27, 28, or 29 in anhydrous DMF (0.1 mL/mg) was treated with K$_2$CO$_3$ (5.0 equiv) and warmed to 85° C. The appropriate dibromide, (R)-30, or (S)-30 (2.5 equiv) was added to the reaction. After stirring for 5 h, reaction was cooled to room temperature and solvent removed with a stream of nitrogen. The resulting residue was purified by flash column chromatography (FCC) to afford the indicated

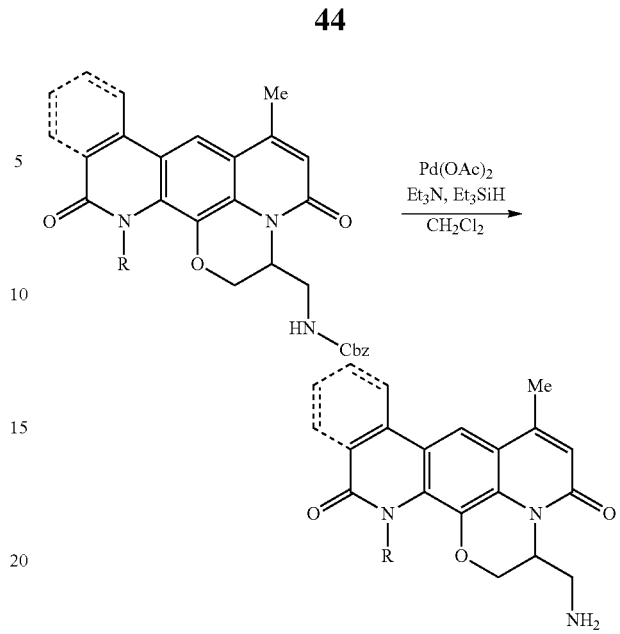

General Procedure B:

A solution of Pd(OAc)$_2$ (0.2 equiv) in anhydrous CH$_2$Cl$_2$ was treated sequentially with Et$_3$N (0.4 equiv) and Et$_3$SiH (3.0 equiv). After 15 minutes, the resulting black solution was transferred to a solution of Cbz-protected amine in CH$_2$Cl$_2$ (10 mM). After stirring at room temperature overnight, reaction was quenched with saturated NH$_4$OH (20 μML) and stirred for an additional 1 h. The solvent was removed in vacuo and the resulting residue purified by FCC.

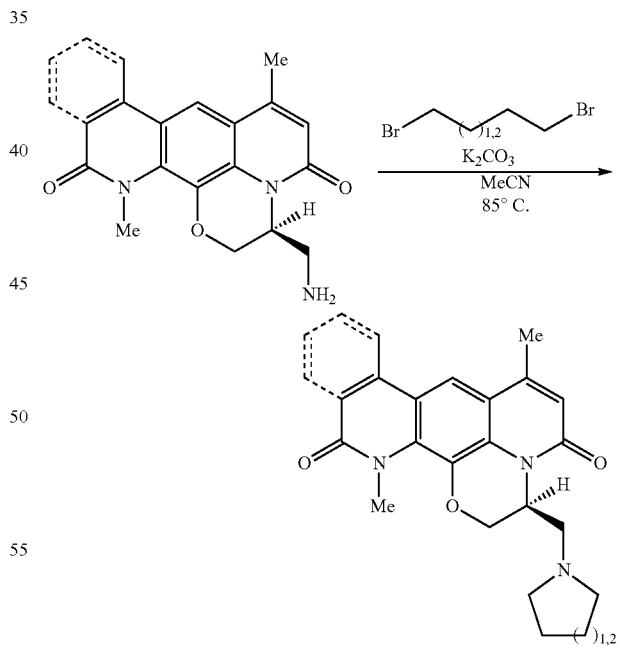

General Procedure C:

To a solution of (S)-6DNM-NH3 (18) or (S)-Ph6DNM-NH3 (16) in MeCN (7.5 mM) was added K$_2$CO$_3$ (2.2 equiv) and 1,4-dibromobutane or 1,5-dibromopentane (1.1 equiv). The reaction was heated to 85° C. overnight. The reaction was cooled to room temperature and concentrated in vacuo. The resulting residue was purified by FCC to yield 20-23.

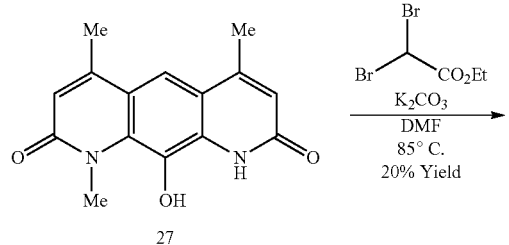

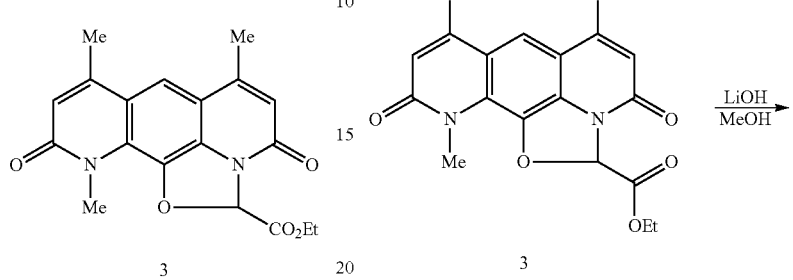

¹H NMR: (500 MHz, CD₄OD/CDCl₃): 7.54 (s, 1H), 6.87 (s, 1H), 6.49 (s, 1H), 6.45 (s, 1H), 3.93 (s, 3H), 2.53 (s, 3H), 2.50 (s, 3H).

¹³C NMR: (126 MHz, CD₄OD/CDCl₃): 165.93, 162.74, 159.50, 149.36, 148.02, 135.47, 132.12, 125.66, 121.42, 121.05, 120.12, 114.29, 114.07, 91.96, 32.85, 20.14, 17.93.

Procedure for 3:
Prepared from 27 (150 mg, 0.554 mmol) and ethyl dibromoacetate according to General Procedure A to yield 3 (39.0 mg, 20%).

¹H NMR: (400 MHz, CDCl₃) δ 7.50 (s, 1H), 6.77 (s, 1H), 6.52 (d, J=1.40 Hz, 1H), 6.46 (d, J=1.31 Hz, 1H), 4.37 (q, J=7.14 Hz, 2H), 3.91 (s, 3H), 2.53 (d, J=1.25 Hz, 3H), 2.50 (d, J=1.18 Hz, 3H), 1.36 (t, J=7.12 Hz, 3H).

¹³C NMR: (126 MHz, CDCl₃) δ 163.74, 161.76, 158.24, 147.98, 146.66, 134.27, 132.07, 125.90, 121.27, 120.66, 120.36, 114.15, 113.19, 91.32, 63.20, 32.52, 20.10, 17.88, 13.95.

HRMS (ESI): m/z calcd for $C_{19}H_{19}N_2O_5$ [M+H]⁺: 355.1294, found 355.1291.

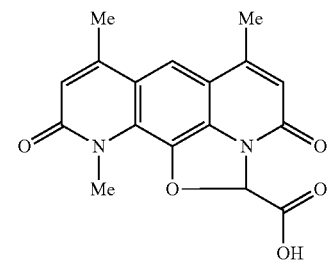

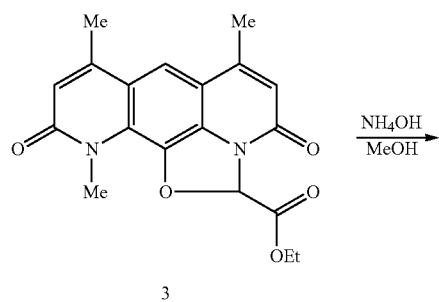

Procedure for 5

A solution of 3 (7.3 mg, 0.0206 mmol) in MeOH (mL) was basified with 2.5 M LiOH (40 µL, 0.100 mmol) and allowed to stir for 3 h. The solvent was removed in vacuo and the resulting residue was redissolved in H₂O (2 mL) and acidified with 6 M HCl until visible precipitate formed and then extracted with CHCl₃ (3×5 mL). The combined organic layers were dried over Na₂SO₂, decanted, and concentrated in vacuo to furnish 5 as a white solid (4.6 mg, 68%).

¹H NMR: (500 MHz, CD₄OD/CDCl₃): 7.51 (s, 1H), 6.72 (s, 1H), 6.47 (s, 1H), 6.44 (s, 1H), 3.89 (s, 3H), 2.51 (s, 3H), 2.48 (s, 3H).

¹³C NMR: (126 MHz, CD₄OD/CDCl₃): 165.35, 162.47, 159.05, 148.81, 147.69, 134.94, 132.08, 125.58, 121.06, 121.00, 119.95, 114.16, 113.76, 92.17, 32.71, 20.03, 17.81.

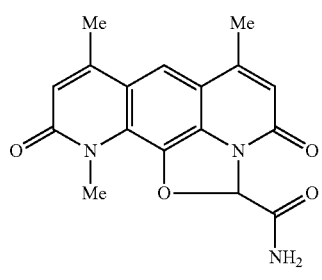

Procedure for 4:
A solution of 3 (7.1 mg, 0.0200 mmol) in MeOH (4 mL) was treated with 30% NH₄OH (0.33 mL, 2.99 mmol) and stirred at room temperature for 3 h. Solvent was then removed in vacuo and resulting residue purified by FCC: 0-5% MeOH/CH₂Cl₂ to yield 4 as a white solid.

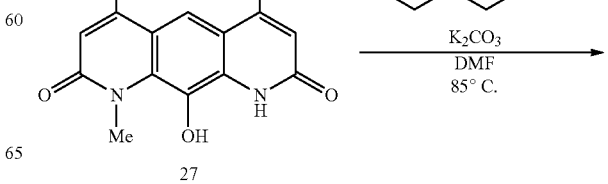

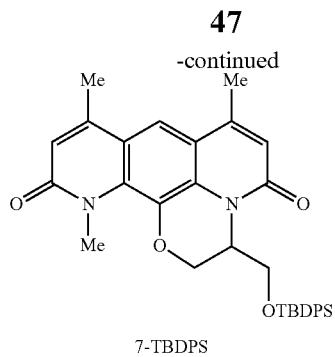

7-TBDPS

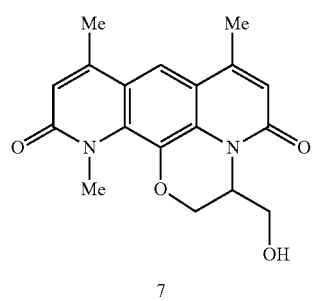

7

Procedure for 7-TBDPS:

Prepared from 27 (50.0 mg, 0.185 mmol) and tert-butyl (2,3-dibromopropoxy)diphenylsilane[4] according to General Procedure A to yield 7-TBDPS (17.3 mg, 16%).

$^1$H NMR: (500 MHz, CDCl$_3$): 7.65 (m, 4H), 7.51 (s, 1H), 7.37 (m, 6H), 6.56 (d, J=1.38 Hz, 1H), 6.50 (q, J=1.16 Hz, 1H), 5.17 (dddd, J=1.04, 2.38, 4.44, 9.68 Hz, 1H), 5.05 (dd, J=1.10, 11.25 Hz, 1H), 4.00 (ddd, J=0.94, 2.53, 11.07 Hz, 1H), 3.94 (ddd, J=1.02, 4.69, 9.38 Hz, 1H), 3.90 (s, 3H), 3.76 (t, J=9.55 Hz, 1H), 2.47 (d, J=1.18 Hz, 3H), 2.46 (d, J=1.19 Hz, 3H), 1.07 (s, 9H).

$^{13}$C NMR: (126 MHz, CDCl$_3$): 163.63, 160.10, 146.81, 145.84, 135.67, 135.60, 133.21, 132.92, 131.23, 130.95, 130.00, 127.92, 127.88, 127.49, 120.88, 120.09, 118.55, 116.96, 113.91, 63.68, 59.84, 50.03, 35.59, 26.96, 19.41, 19.20.

Procedure for 7:

A flame-dried RBF was charged with 7-TBDPS (16.4 mg, 0.0290) and THF (3 mL) and cooled to 0° C. A 1M solution of TBAF (0.06 mL, 0.06 mmol) was added and the reaction was allowed to warm to room temperature over 90 min. Reaction was then quenched with 6 M HCl (20 µL) and concentrated in vacuo. The resulting residue was purified by FCC eluting with 0-5% MeOH/CH$_2$Cl$_2$ to yield 7 as a white solid (8.4 mg, 89%).

$^1$H NMR: (500 MHz, CDCl$_3$): 7.59 (s, 1H), 6.58 (d, J=1.35 Hz, 1H), 6.58 (d, J=1.10 Hz, 1H), 5.12 (dddd, J=1.20, 2.65, 6.32, 7.56 Hz, 1H), 4.88 (dd, J=1.20, 11.49 Hz, 1H), 4.01 (dd, J=2.58, 11.42 Hz, 1H), 3.96 (m, 1H), 3.96 (s, 3H), 3.89 (m, 1H), 2.84 (bs, 1H), 2.54 (d, J=1.19 Hz, 3H), 2.49 (d, J=1.29 Hz, 3H).

$^{13}$C NMR: (126 MHz, CDCl$_3$): 163.60, 161.24, 147.46, 145.83, 131.19, 131.17, 127.35, 121.13, 119.86, 118.86, 117.12, 114.29, 64.27, 61.46, 51.03, 35.62, 19.41, 19.26.

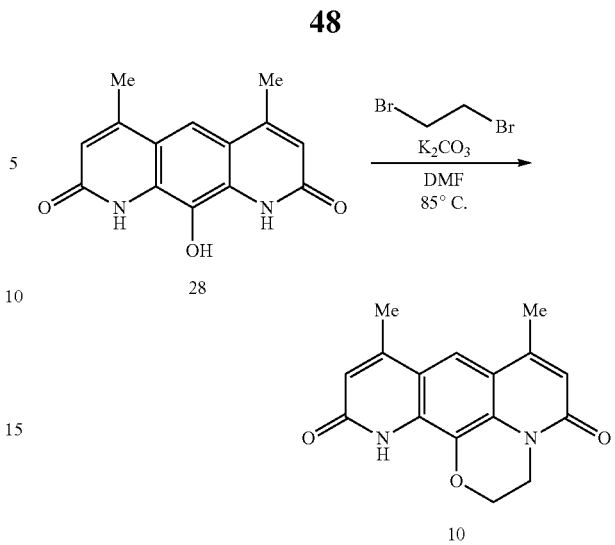

Procedure for 10:

Prepared from 28 (100.0 mg, 0.3902 mmol) according to General Procedure A modified by using 1.05 equiv 1,2-dibromoethane and 3.00 equiv K$_2$CO$_3$ to yield 10 (53.5 mg, 49%).

$^1$H NMR: (500 MHz, MeOD/CDCl$_3$): 7.66 (s, 1H), 6.52 (d, J=1.34 Hz, 1H), 6.48 (d, J=1.42 Hz, 1H), 4.53 (t, J=4.80 Hz, 2H), 4.29 (dd, J=4.19, 5.36 Hz, 2H), 2.56 (d, J=1.19 Hz, 3H), 2.55 (d, J=1.15 Hz, 3H).

$^{13}$C NMR: (126 MHz, MeOD/CDCl$_3$): 163.74, 161.44, 150.33, 148.96, 129.36, 128.24, 126.65, 120.54, 119.62, 117.83, 117.35, 114.03, 64.77, 40.55, 19.31, 19.29.

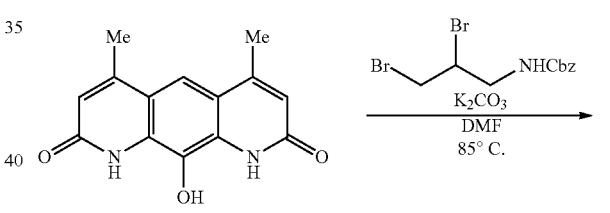

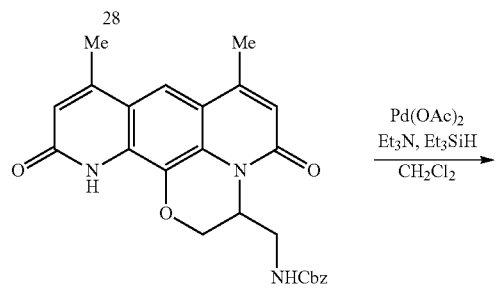

11-Cbz

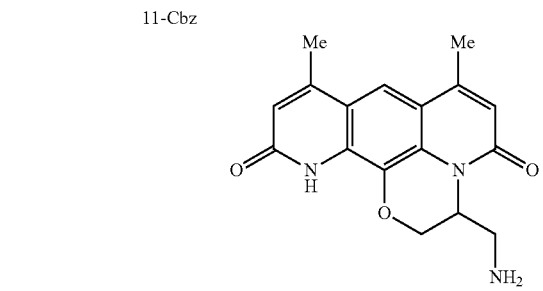

11

Procedure for 11-Cbz:

Prepared from 28 (255 mg, 0.993 mmol) according to General Procedure A modified by using 1.05 equiv benzyl (2,3-dibromopropyl)carbamate and 3.00 equiv $K_2CO_3$ to yield 11-Cbz (85.4 mg, 19% yield).

$^1$H NMR: (500 MHz, $CDCl_3$): 8.96 (s, 1H), 7.49 (s, 1H), 7.25 (m, 5H), 6.44 (m, 2H), 5.35 (t, J=5.83 Hz, 1H), 5.08 (t, J=7.29 Hz, 1H), 4.97 (s, 2H), 4.70 (d, J=11.55 Hz, 1H), 4.06 (m, 1H), 3.59 (dt, J=6.34, 15.06 Hz, 1H), 3.45 (dt, J=6.44, 13.53 Hz, 1H), 2.45 (s, 3H), 2.44 (s, 3H).

$^{13}$C NMR: (126 MHz, $CDCl_3$): 161.77, 160.53, 156.67, 148.37, 147.69, 136.46, 128.63, 128.21, 128.04, 127.44, 125.59, 121.05, 119.74, 116.87, 116.46, 113.69, 67.03, 65.90, 48.92, 42.19, 29.86, 19.35, 19.29.

Procedure for 11:

Prepared from 11-Cbz (9.0 mg, 0.0202 mmol) according to General Procedure B to yield 11 (5.9 mg, 94% yield).

$^1$H NMR: (500 MHz, $CD_3OD/CDCl_3$): 7.69 (s, 1H), 6.53 (d, J=1.40 Hz, 1H), 6.49 (d, J=1.36 Hz, 1H), 4.97 (d, J=11.62 Hz, 1H), 4.93 (m, 1H), 4.13 (dd, J=2.37, 11.62 Hz, 1H), 2.93 (m, 2H), 2.57 (s, 2H), 2.56 (s, 4H).

$^{13}$C NMR: (126 MHz, $CD_3OD/CDCl_3$): 163.75, 161.30, 150.24, 149.18, 129.03, 128.33, 125.95, 120.65, 119.72, 117.88, 117.38, 114.31, 65.15, 51.71, 41.35, 19.33, 19.30.

$^1$H NMR: (500 MHz, $CDCl_3$): 7.59 (s, 1H), 6.57 (d, J=1.28 Hz, 1H), 6.56 (d, J=1.48 Hz, 1H), 5.45 (bs, 1H), 4.65 (t, J=6.04 Hz, 2H), 4.48 (t, J=4.83 Hz, 2H), 4.31 (dd, J=4.02, 5.53 Hz, 2H), 3.64 (q, J=5.94 Hz, 2H), 2.52 (d, J=1.28 Hz, 3H), 2.50 (d, J=1.15 Hz, 3H), 1.40 (s, 9H).

$^{13}$C NMR: (126 MHz, $CDCl_3$): 164.30, 160.52, 156.26, 146.74, 146.60, 131.00, 130.29, 128.20, 120.66, 120.24, 118.76, 117.21, 114.35, 79.14, 63.96, 46.85, 42.14, 40.08, 28.55, 19.60, 19.17.

Procedure for 12:

A 20 mL vial containing 12-Boc (10.2 mg, 0.0240 mmol) in a mixture of EtOAc and MeOH (4 mL, 1:1) was acidified with 3 M HCl (2 mL). After 6 h, the reaction was neutralized with saturated NaHCO3 and concentrated in vacuo. The resulting residue was purified by FCC eluting with 1:1:8 $NH_4OH/MeOH/CHCl_3$ to yield 12 as a white solid (6.3 mg, 81% yield).

1H NMR: (500 MHz, $CDCl_3$): 7.60 (s, 1H), 6.57 (m, 2H), 4.63 (m, 2H), 4.43 (t, J=4.82 Hz, 2H), 4.32 (m, 2H), 3.12 (m, 2H), 2.53 (d, J=1.20 Hz, 3H), 2.49 (d, J=1.18 Hz, 3H). $^{13}$C NMR: (126 MHz, $CDCl_3$): 163.81, 160.55, 146.70, 146.16, 130.85, 130.33, 128.12, 120.95, 120.05, 118.83, 117.02, 114.54, 63.98, 49.65, 42.69, 40.12, 19.60, 19.20

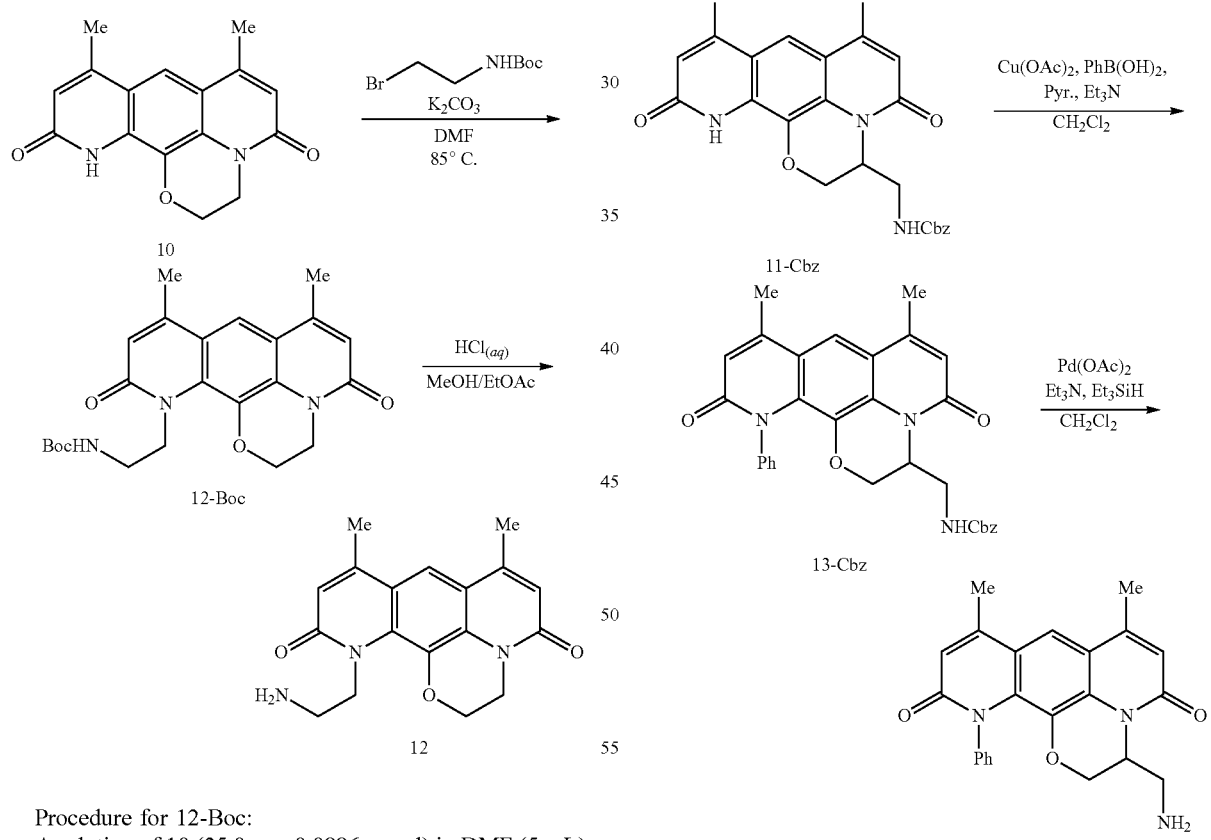

Procedure for 12-Boc:

A solution of 10 (25.0 mg, 0.0886 mmol) in DMF (5 mL) was cooled to 0° C. in an ice bath. To the reaction was added KO$^t$Bu (21.6 mg, 0.177 mmol) and allowed to stir for 10 min. The resulting yellow solution was treated with tert-butyl (2-bromoethyl)carbamate (39.7 mg, 0.177 mmol) and allowed to warm to room temperature overnight before being concentrated with a stream of air. The result residue was purified by FCC eluting with 90% EtOAc/Hex to yield 12-Boc as an off-white solid (10.2 mg, 27%).

Procedure for 13-Cbz:

A flame-dried 15 mL RBF was charged with 11-Cbz (15.0 mg, 0.0337 mmol), PhB(OH)$_2$ and Cu(OAc)$_2$ (12.2 mg, 0.0673 mmol). The solids were dissolved in $CH_2Cl_2$ (5 mL) and treated with Et3N (9.3 µL, 0.067 mmol) and pyridine (5.4 µL, 0.067 mmol). After 48 h, reaction was concentrated in vacuo and residue purified by FCC (95% EtOAc/Hex-100% EtOAc-2.5% MeOH/EtOAc) to yield 13-Cbz (4.2 mg, 24% yield) and 11-Cbz (8.9 mg, 59%).

HRMS (ESI): m/z calcd for $C_{31}H_{28}N_3O_5$ $[M+H]^+$: 522.2029, found 522.2014.

Procedure for 13:

Synthesized from 13-Cbz according to General Procedure B to yield 13 (4.2 mg, 24% yield).

HRMS (ESI): m/z calcd for $C_{31}H_{28}N_3O_5$ $[M+H]^+$: 522.2029, found 522.2014.

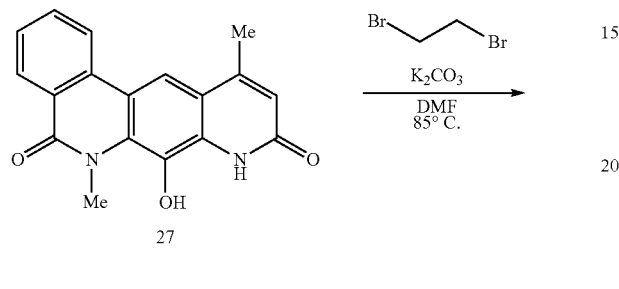

27

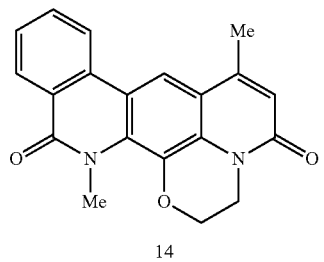

14

Procedure for 14:

Synthesized from 27 (16.9 mg, 0.0552 mmol) and 1,2-dibromoethane according to General Procedure B to yield 14 (9.2 mg, 50% yield).

$^1$H NMR: (400 MHz, CDCl$_3$) δ 8.50 (dd, J=1.40, 7.94 Hz, 1H), 8.23 (dd, J=0.99, 8.07 Hz, 1H), 8.15 (s, 1H), 7.75 (ddd, J=1.47, 7.14, 8.32 Hz, 1H), 7.57 (ddd, J=1.02, 7.15, 8.02 Hz, 1H), 6.58 (d, J=1.23 Hz, 1H), 4.44 (dd, J=4.23, 5.37 Hz, 2H), 4.32 (dd, J=4.12, 5.43 Hz, 2H), 3.98 (s, 3H), 2.59 (d, J=1.21 Hz, 3H).

$^{13}$C NMR: (126 MHz, CDCl$_3$) δ 163.24, 160.31, 146.63, 133.19, 132.66, 131.89, 129.27, 128.96, 128.04, 127.40, 125.20, 121.39, 119.94, 117.17, 116.43, 111.80, 63.80, 39.94, 36.84, 19.17.

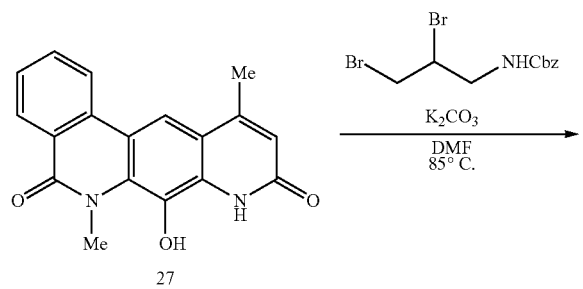

27

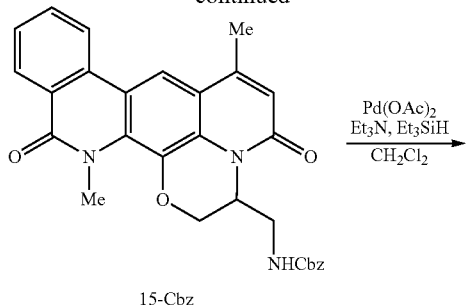

15-Cbz

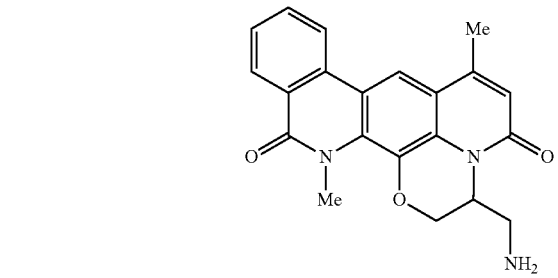

15

Procedure for 15-Cbz:

Prepared from 29 (40.0 mg, 0.1306 mmol) and benzyl (2,3-dibromopropyl)carbamate according to General Procedure A to yield 15-Cbz as an off-white solid (11.5 mg, 18%).

$^1$H NMR: (400 MHz, CDCl$_3$): 8.51 (dd, J=1.52, 7.98 Hz, 1H), 8.23 (d, J=8.17 Hz, 1H), 8.17 (s, 1H), 7.76 (td, J=1.47, 7.75, 8.25 Hz, 1H), 7.58 (ddd, J=1.17, 7.06, 8.12 Hz, 1H), 7.33 (m, 5H), 6.56 (d, J=1.30 Hz, 1H), 5.59 (t, J=5.74 Hz, 1H), 5.13 (m, 2H), 5.06 (d, J=5.48 Hz, 2H), 4.75 (d, J=11.37 Hz, 1H), 4.04 (d, J=11.49 Hz, 1H), 3.99 (s, 3H), 3.76 (dt, J=6.22, 13.05 Hz, 1H), 3.59 (dt, J=6.28, 13.40 Hz, 1H), 2.59 (d, J=1.42 Hz, 3H).

$^{13}$C NMR: (126 MHz, CDCl$_3$): 163.32, 160.78, 156.75, 147.42, 136.50, 133.22, 132.83, 131.64, 129.63, 129.13, 128.60, 128.30, 128.24, 128.18, 126.58, 125.40, 121.57, 119.90, 117.33, 116.77, 112.22, 66.98, 65.55, 48.86, 42.42, 37.03, 19.36.

HRMS (ESI): m/z calcd for $C_{29}H_{26}N_3O_5$ $[M+H]^+$: 496.1872, found 496.1866.

Procedure for 15:

Prepared from 15-Cbz (11.5 mg, 0.0232 mmol) according to General Procedure B to yield 15 as a white solid (7.8 mg, 93% yield).

$^1$H NMR: (400 MHz, CDCl$_3$) δ 8.51 (dd, J=1.46, 7.99 Hz, 1H), 8.24 (d, J=8.98 Hz, 1H), 8.17 (s, 1H), 7.76 (ddd, J=1.49, 7.16, 8.38 Hz, 1H), 7.58 (ddd, J=1.04, 7.16, 8.06 Hz, 1H), 6.59 (d, J=1.46 Hz, 1H), 4.95 (m, 2H), 4.03 (m, 1H), 4.00 (s, 3H), 3.14 (dd, J=5.24, 12.72 Hz, 1H), 3.02 (dd, J=8.63, 12.74 Hz, 1H), 2.60 (d, J=1.22 Hz, 3H), 1.87 (br, 2H).

$^{13}$C NMR: (126 MHz, CDCl$_3$) δ 163.40, 160.44, 146.96, 133.31, 132.83, 131.81, 129.46, 129.13, 128.23, 126.98, 125.38, 121.56, 120.23, 117.38, 116.60, 112.06, 64.53, 51.07, 41.52, 37.06, 19.35.

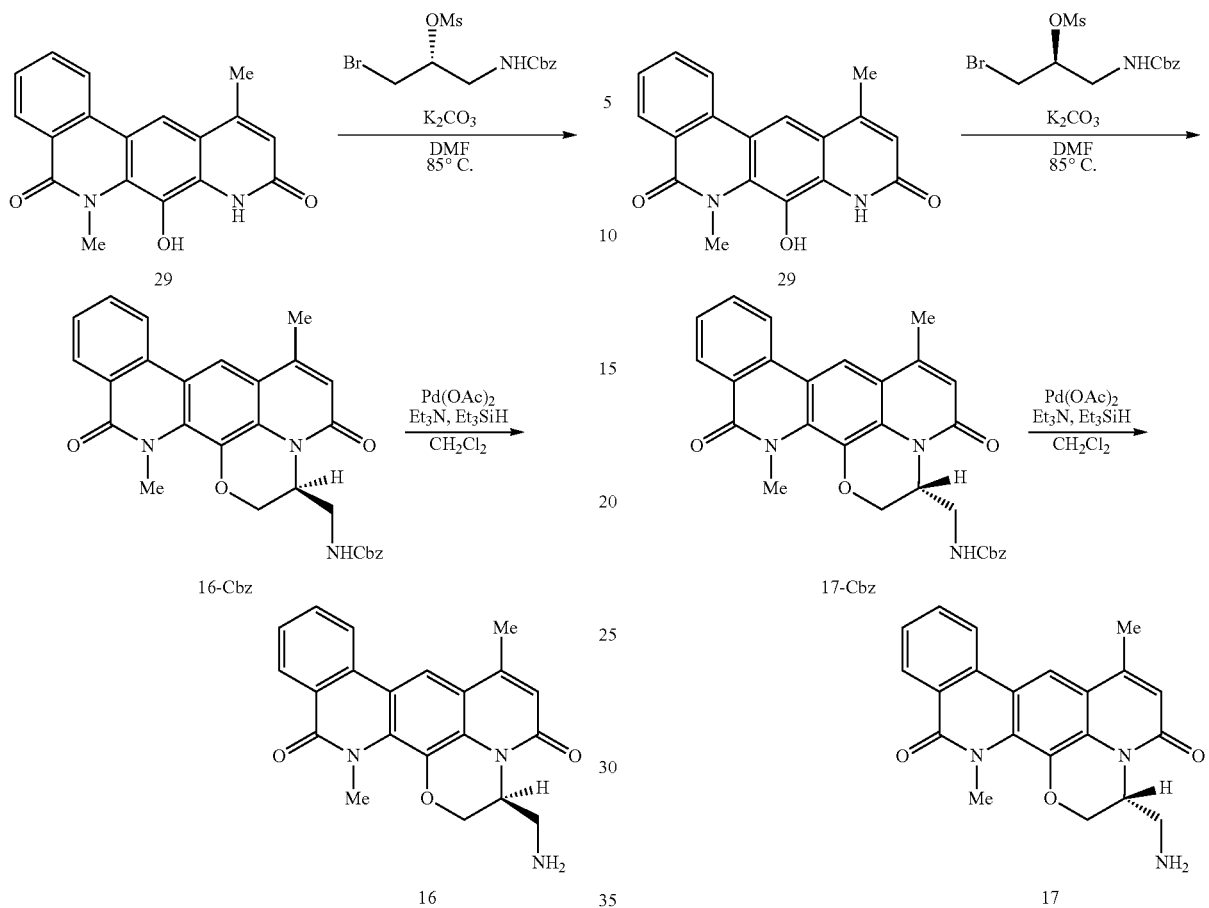

Procedure for 16-Cbz:

Prepared from 29 (82.2 mg, 0.268 mmol) and (R)-30 according to General Procedure A to yield 16-Cbz (31.3 mg, 24% yield).

$^1$H NMR: (400 MHz, CDCl$_3$): 8.51 (dd, J=1.43, 7.92 Hz, 1H), 8.24 (d, J=8.18 Hz, 1H), 8.17 (s, 1H), 7.76 (m, 1H), 7.58 (t, J=7.56 Hz, 1H), 7.33 (m, 5H), 6.56 (d, J=1.44 Hz, 1H), 5.59 (t, J=5.88 Hz, 1H), 5.13 (m, 2H), 5.06 (d, J=5.79 Hz, 2H), 4.75 (d, J=11.37 Hz, 1H), 4.04 (m, 1H), 3.99 (s, 3H), 3.76 (dt, J=6.00, 11.89 Hz, 1H), 3.59 (dt, J=6.24, 13.08 Hz, 1H), 2.59 (s, 3H).

$^{13}$C NMR: (126 MHz, CDCl$_3$) δ 163.32, 160.78, 156.74, 147.41, 136.49, 133.21, 132.83, 131.64, 129.62, 129.13, 128.60, 128.30, 128.24, 128.18, 126.57, 125.39, 121.57, 119.90, 117.33, 116.76, 112.22, 66.97, 65.55, 48.84, 42.43, 37.04, 19.37.

Procedure for 16:

Prepared from 16-Cbz (31.3 mg, 0.0632 mmol) according to General Procedure B to yield 16 as a white solid (21.5 mg, 94% yield).

$^1$H NMR: (400 MHz, CDCl$_3$) δ 8.51 (ddd, J=0.59, 1.48, 7.95 Hz, 1H), 8.25 (d, J=8.30 Hz, 1H), 8.18 (s, 1H), 7.76 (ddd, J=1.48, 7.14, 8.33 Hz, 1H), 7.58 (ddd, J=1.02, 7.16, 8.07 Hz, 1H), 6.59 (d, J=1.26 Hz, 1H), 4.95 (dd, J=1.09, 11.24 Hz, 1H), 4.91 (m, 1H), 4.03 (ddd, J=0.99, 2.51, 11.22 Hz, 1H), 4.00 (s, 3H), 3.12 (m, 1H), 2.99 (dd, J=8.87, 12.74 Hz, 1H), 2.60 (d, J=1.19 Hz, 3H).

$^{13}$C NMR: (126 MHz, CDCl$_3$) δ 163.41, 160.38, 146.90, 133.33, 132.83, 131.82, 129.44, 129.13, 128.22, 127.01, 125.38, 121.56, 120.26, 117.37, 116.58, 112.04, 64.45, 51.17, 41.47, 37.06, 19.34.

Procedure for 17-Cbz:

Prepared from 29 (20.4 mg, 0.0666 mmol) and (S)-30 according to General Procedure A to yield 17-Cbz (10.2 mg, 31% yield).

$^1$H NMR: (400 MHz, CDCl$_3$) 8.52 (m, 1H), 8.24 (d, J=8.22 Hz, 1H), 8.18 (s, 1H), 7.77 (dt, J=1.49, 7.58 Hz, 1H), 7.58 (t, J=7.57 Hz, 1H), 7.30 (m, 5H), 6.57 (d, J=1.57 Hz, 1H), 5.54 (bs, J=5.74 Hz, 1H), 5.13 (dd, J=5.10, 8.02 Hz, 1H), 5.06 (d, J=6.18 Hz, 2H), 4.75 (d, J=11.43 Hz, 1H), 4.04 (dd, J=2.67, 11.49 Hz, 1H), 4.00 (s, 3H), 3.76 (dq, J=3.60, 4.88, 9.72 Hz, 1H), 3.60 (dt, J=6.31, 13.42 Hz, 1H), 2.59 (s, 3H).

$^{13}$C NMR: (126 MHz, CDCl$_3$): 163.34, 160.80, 156.74, 147.41, 136.50, 133.24, 132.84, 131.65, 129.66, 129.16, 128.61, 128.32, 128.25, 128.19, 126.60, 125.43, 121.58, 119.93, 117.34, 116.79, 112.25, 66.99, 65.60, 48.85, 42.50, 37.04, 19.38.

Procedure for 17:

Prepared from 17-Cbz (10.2 mg, 0.0206 mmol) according to General Procedure B to yield 17 as a white solid (7.0 mg, 94% yield).

$^1$H NMR: (400 MHz, CDCl$_3$) δ 8.52 (dd, J=1.61, 7.99 Hz, 1H), 8.25 (d, J=8.53 Hz, 1H), 8.18 (s, 1H), 7.77 (ddd, J=1.48, 7.17, 8.36 Hz, 1H), 7.58 (ddd, J=1.04, 7.14, 8.13 Hz, 1H), 6.59 (d, J=1.23 Hz, 1H), 4.95 (dd, J=1.09, 11.28 Hz, 1H), 4.91 (m, 1H), 4.03 (ddd, J=0.94, 2.50, 11.25 Hz, 1H), 4.00 (s, 3H), 3.13 (ddd, J=1.10, 5.14, 12.83 Hz, 1H), 2.99 (dd, J=8.93, 12.74 Hz, 1H), 2.60 (d, J=1.22 Hz, 3H).

$^{13}$C NMR: (126 MHz, CDCl$_3$) δ 163.42, 160.38, 146.89, 133.33, 132.84, 131.82, 129.45, 129.14, 128.23, 127.02, 125.39, 121.57, 120.27, 117.37, 116.58, 112.04, 64.44, 51.18, 41.46, 37.06, 19.34.

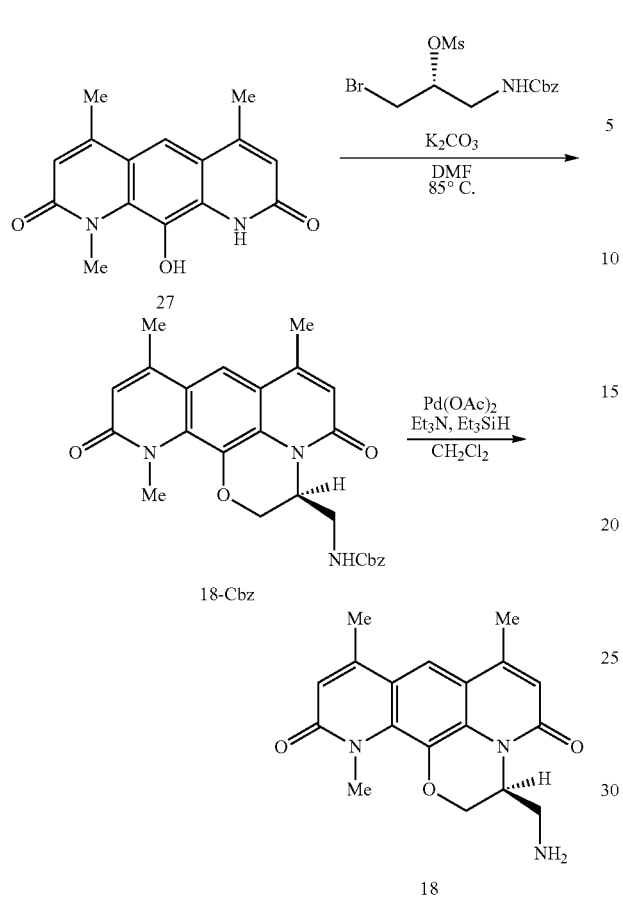

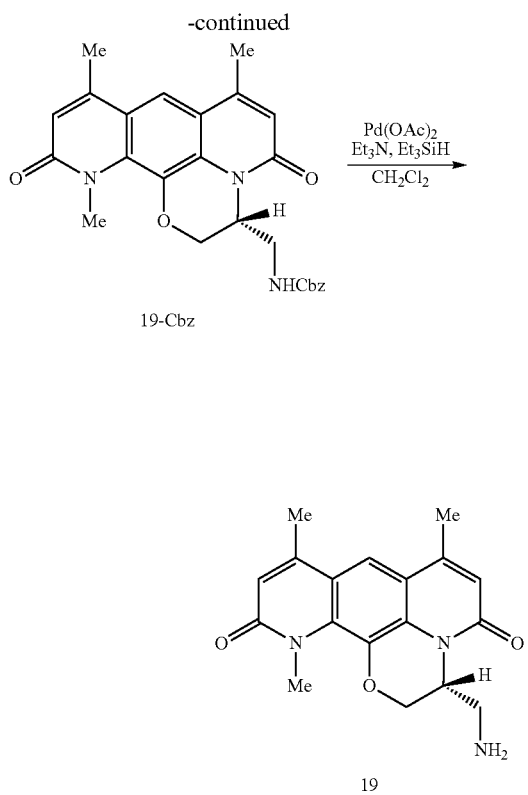

Procedure for 18-Cbz:

Prepared from 27 (14.8 mg, 0.0546 mmol) and (R)-30 according to General Procedure A to yield 18-Cbz (19.1 mg, 67% yield).

$^1$H NMR: (400 MHz, CDCl$_3$): 7.56 (s, 1H), 7.30 (m, 5H), 6.57 (d, J=1.55 Hz, 1H), 6.53 (d, J=1.48 Hz, 1H), 5.68 (bs, 1H), 5.11 (td, J=2.46, 6.80 Hz, 1H), 5.05 (d, J=3.62 Hz, 2H), 4.73 (d, J=11.51 Hz, 1H), 3.98 (d, J=10.11 Hz, 1H), 3.95 (s, 3H), 3.71 (dt, J=6.42, 13.70 Hz, 1H), 3.55 (dt, J=6.18, 13.70 Hz, 1H), 2.50 (s, 3H), 2.47 (s, 3H).

$^{13}$C NMR: (126 MHz, CDCl$_3$): 163.55, 160.79, 156.74, 147.35, 145.78, 136.50, 131.19, 130.99, 128.57, 128.20, 128.12, 126.97, 121.07, 119.77, 118.80, 117.03, 114.24, 66.92, 65.33, 48.83, 42.18, 35.61, 19.37, 19.22.

Procedure for 18:

Prepared from 18-Cbz (22.8 mg, 0.0496 mmol) according to General Procedure B to yield 18 as a white solid (15.8 mg, 98% yield).

Procedure for 19-Cbz:

Prepared from 27 (14.8, 0.0546 mmol) and (S)-30 according to General Procedure A to yield 19-Cbz (13.3 mg, 53% yield).

$^1$H NMR: (400 MHz, CDCl$_3$) 7.57 (s, 1H), 7.31 (m, 5H), 6.58 (s, 1H), 6.53 (d, J=1.48 Hz, 1H), 5.59 (bs, 1H), 5.12 (m, 1H), 5.05 (d, J=4.87 Hz, 2H), 4.73 (d, J=11.36 Hz, 1H), 4.00 (dd, J=3.00, 12.26 Hz, 1H), 3.96 (s, 3H), 3.72 (dt, J=6.21, 13.12 Hz, 1H), 3.56 (dt, J=6.23, 13.52 Hz, 1H), 2.51 (s, 3H), 2.48 (s, 3H).

$^{13}$C NMR: (126 MHz, CDCl$_3$): 163.56, 160.83, 156.72, 147.36, 145.79, 136.50, 131.24, 130.99, 128.60, 128.24, 128.16, 127.00, 121.12, 119.81, 118.83, 117.05, 114.29, 66.97, 65.41, 48.83, 42.34, 35.64, 19.40, 19.25.

Procedure for 19:

Prepared from 19-Cbz (10.1 mg, 0.0220 mmol) according to General Procedure B to yield 19 as a white solid (6.9 mg, 96% yield).

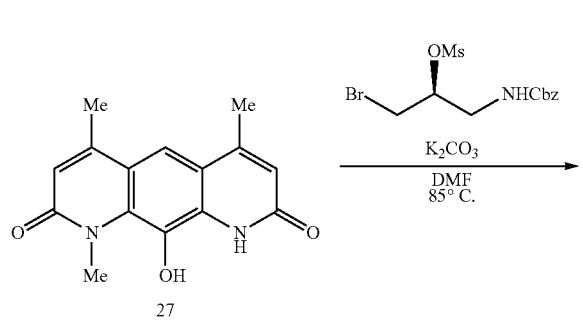

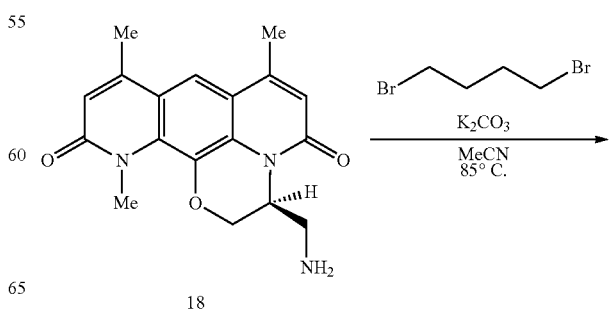

57

-continued

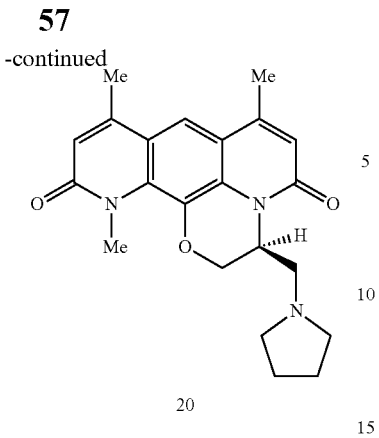

20

Procedure for 20:

Prepared from 18 (10.0 mg, 0.0341 mmol) and 1,4-dibromobutane according to General Procedure C to yield 20 (10.1 mg, 78% yield).

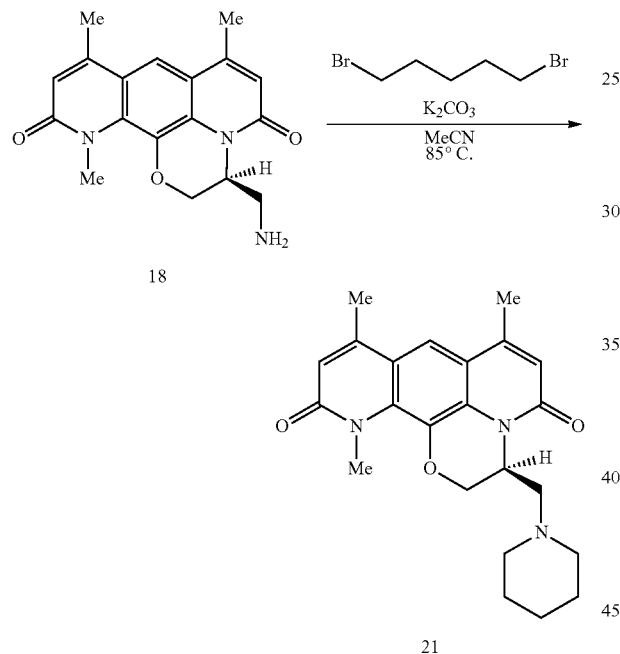

Procedure for 21:

Prepared from 18 (20.0 mg, 0.0615 mmol) and 1,5-dibromopentane according to General Procedure C to yield 23 (15.5 mg, 64% yield).

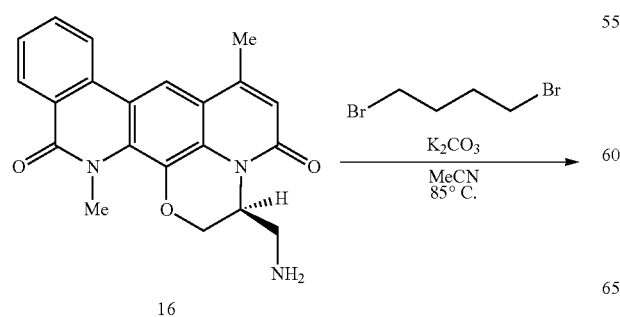

58

-continued

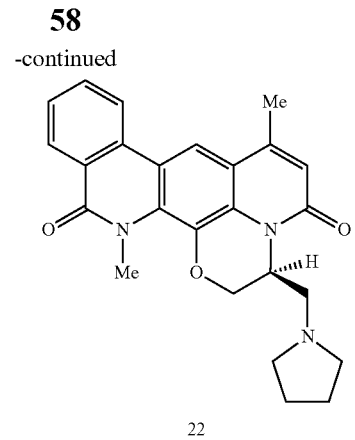

22

Procedure for 22:

Prepared from 16 (21.5 mg, 0.0595 mmol) and 1,4-dibromobutane according to General Procedure C to yield 22 (11.9 mg, 48% yield).

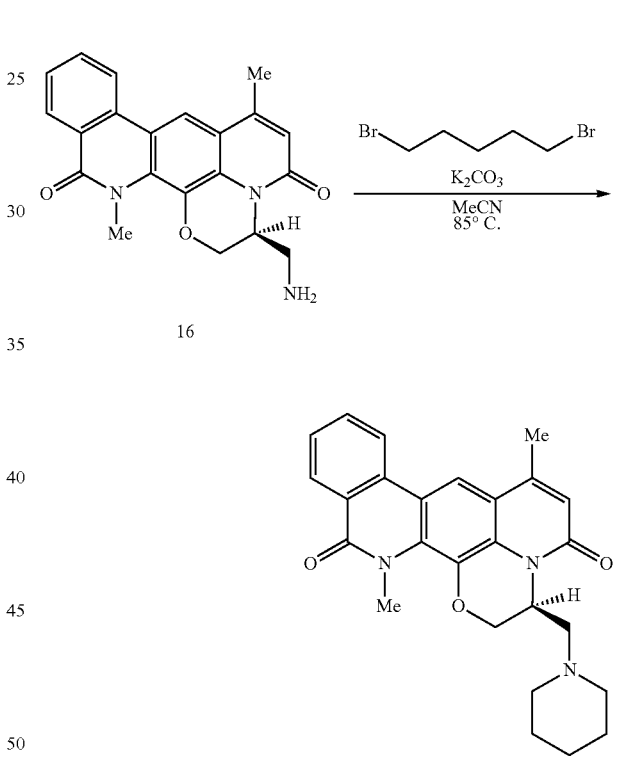

Procedure for 23:

Prepared from 16 (12.3 mg, 0.0339 mmol) and 1,5-dibromopentane according to General Procedure C to yield 23 (10.4 mg, 71% yield).

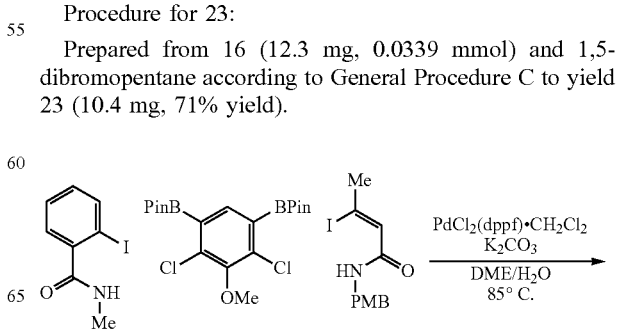

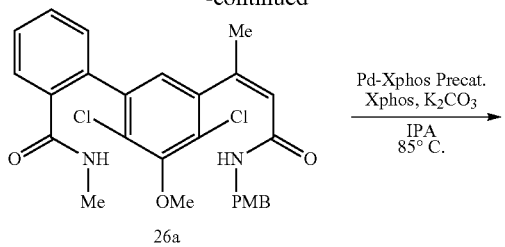

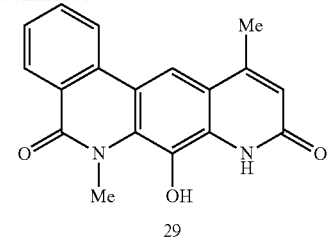

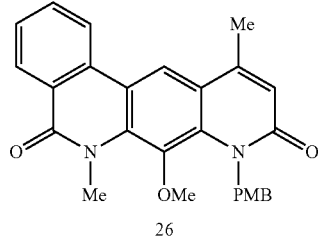

Procedure for 29:

A 100 mL RBF was charged with 26 (420 mg, 0.953 mmol) and 48% HBr (40 mL). The suspension was heated to reflux overnight then cooled to room temperature. Solvent was removed in vacuo and resulting solid was azeotroped with toluene (3×) to yield 29 (290 mg, 99% yield). Solid used in subsequent reactions without further purification.

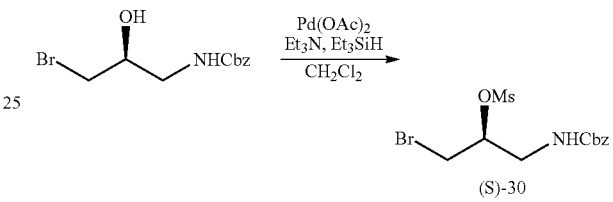

Procedure for 26:

An oven-dried RBF was charged with 2-iodo-N-methylbenzamide (2.500 g, 9.576 mmol), 2,2'-(4,6-dichloro-5-methoxy-1,3-phenylene)bis(4,4,5,5-tetramethyl-1,3,2-dioxaborolane) (2.011 g, 4.688 mmol), (Z)-3-iodo-N-(4-methoxybenzyl)but-2-enamide (3.171 g, 9.576 mmol), PdCl$_2$(dppf).CH$_2$Cl$_2$ (1.203 g, 1.473 mmol), and K$_2$CO$_3$ (6.109 g, 44.20 mmol). To this mixture was added DME (60 mL) and H$_2$O (6 mL) which had been degassed with nitrogen sparging. The reaction was heated to 85° C. for 5 h then cooled to room temperature. The reaction mixture was then diluted with EtOAc (30 mL) and H$_2$O (100 mL). The aqueous layer was separated and extracted with EtOAc (2×100 mL). The combined organic layers were rinsed with brine (150 mL), dried over Na$_2$SO$_4$ and concentrated in vacuo. The residue was purified via FCC eluting with 65% EtOAc/Hex to yield 26a as beige solid (993 mg, 41% yield).

To an oven-dried RBF was added 26a (993 mg, 1.93 mmol), PdXphos Precatalyst I (160 mg, 0.193 mmol), XPhos (92.2 mg, 0.193 mmol), K$_2$CO$_3$ (1.603 g, 11.59 mmol), and nitrogen-sparged isopropyl alcohol (75 mL). The reaction was heated to 85° C. for 24 h then filtered through Celite. The solvent was removed in vacuo and the residue was purified by FCC eluting with 60% EtOAc/Hex to yield 26 (420 mg, 49% yield).

$^1$H NMR: (400 MHz, CDCl$_3$) δ 8.48 (dd, J=1.37, 8.00 Hz, 1H), 8.22 (s, 1H), 8.21 (m, 1H), 7.76 (ddd, J=1.45, 7.19, 8.35 Hz, 1H), 7.57 (ddd, J=1.03, 7.20, 8.06 Hz, 1H), 7.12 (m, 2H), 6.75 (m, 2H), 6.68 (d, J=1.26 Hz, 1H), 6.05 (bs, 1H), 5.44 (d, J=15.06 Hz, 1H), 3.72 (s, 3H), 3.70 (s, 3H), 3.27 (bs, 3H), 2.60 (d, J=1.20 Hz, 3H).

$^{13}$C NMR: (126 MHz, CDCl$_3$) δ 164.17, 163.80, 158.58, 146.42, 137.33, 135.52, 133.24, 132.99, 130.35, 129.04, 128.51, 128.27, 125.34, 121.44, 120.96, 119.87, 117.36, 114.97, 113.65, 62.00, 55.33, 48.84, 37.22, 19.50.

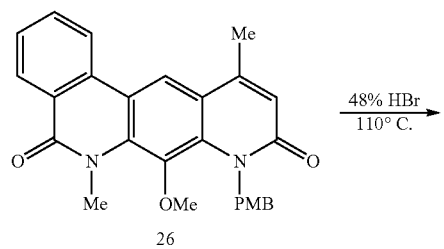

Procedure for (S)-30.

An oven-dried 25 mL RBF was charged with (S)-benzyl (3-bromo-2-hydroxypropyl)carbamate[5] (628 mg, 2.18 mmol) and anhydrous CH$_2$Cl$_2$ (10 mL) and cooled to 0° C. To the solution was sequentially added Et$_3$N (1.2 mL, 8.72 mmol) and MsCl (0.34 mL, 4.35 mmol). After stirring at 0° C., reaction was diluted with CH$_2$Cl$_2$ (20 mL) and 1 M HCl (30 mL). The aqueous layer was extracted with CH$_2$Cl$_2$ (2×30 mL). The combined organic layers were washed with NaHCO$_3$ (30 mL) and brine (30 mL) then dried over Na$_2$SO$_4$. The solvent was removed in vacuo and the residue purified by FCC eluting with 40% EtOAc/Hex to yield (S)-30 as a white solid (738 mg, 93% yield). Solid can be further purified via recrystallization in Et$_2$O.

$^1$H NMR: (400 MHz, CDCl$_3$): 7.36 (m, 5H), 5.24 (bs, 1H), 5.11 (s, 2H), 4.89 (m, 1H), 3.62 (m, 2H), 3.52 (m, 2H), 3.05 (s, 3H).

$^{13}$C NMR: (126 MHz, CDCl$_3$): 156.65, 136.20, 128.71, 128.45, 128.33, 79.12, 67.36, 43.76, 38.61, 30.97.

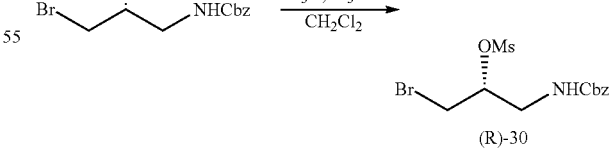

Procedure for (R)-30.

Prepared in an analogous fashion to (S)-30 starting from (R)-benzyl (3-bromo-2-hydroxypropyl)carbamate.

$^1$H NMR: (400 MHz, CDCl$_3$): 7.36 (m, 5H), 5.16 (bs, 1H), 5.12 (s, 2H), 4.90 (m, 1H), 3.63 (m, 2H), 3.54 (m, 2H), 3.06 (s, 3H).

$^{13}$C NMR: (126 MHz, CDCl$_3$): □156.65, 136.20, 128.73, 128.48, 128.36, 79.12, 67.41, 43.81, 38.66, 30.94.

Example 2. General Synthesis of Disclosed Compounds

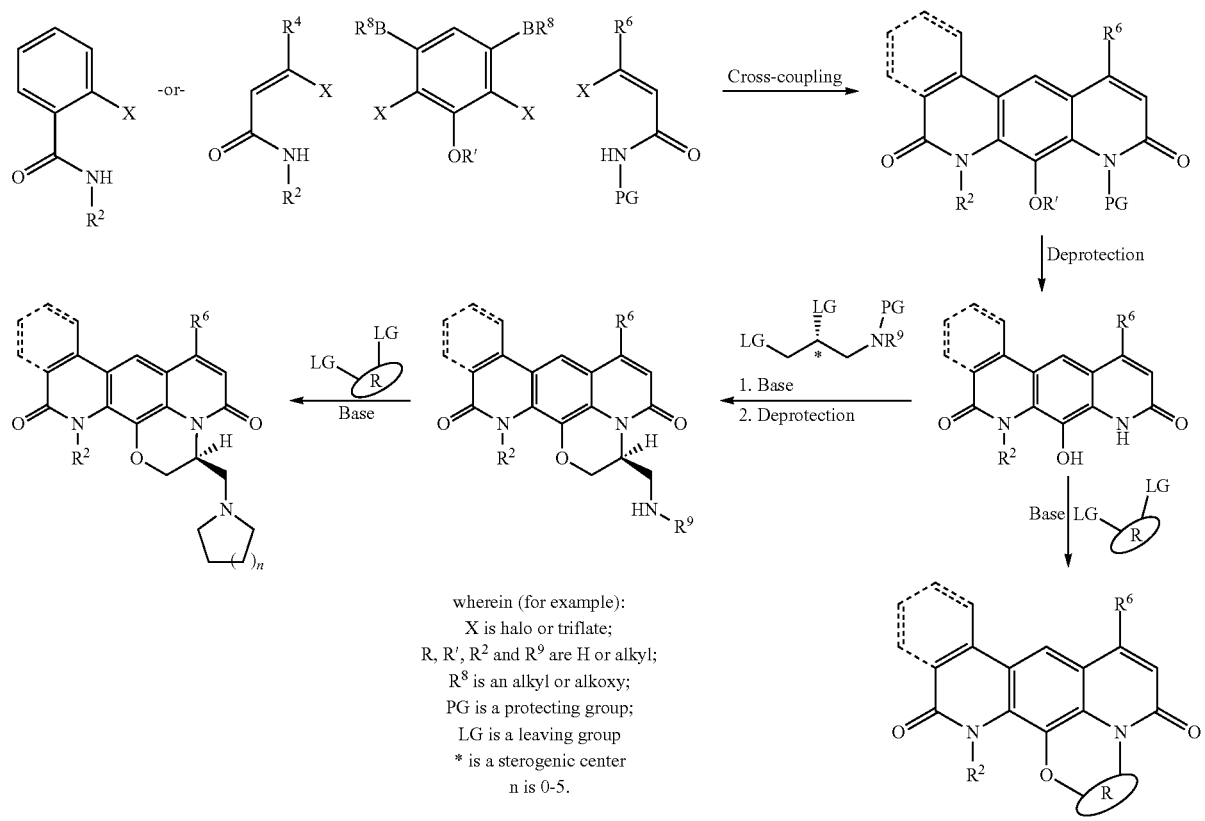

wherein (for example):
X is halo or triflate;
R, R', R$^2$ and R$^9$ are H or alkyl;
R$^8$ is an alkyl or alkoxy;
PG is a protecting group;
LG is a leaving group
* is a sterogenic center
n is 0-5.

Cross-coupling, for example with a transition metal catalyst, of the boron substituted aryl core with one or more vinyl halide or aryl halide reagent afford the tricyclic or tetracyclic heterocycle. When appropriate, functional groups are deprotected. Bis-alkylation with a non-chiral or chiral alkylating reagent, having optional functional groups such as an amine, forms an additional ring moiety on the heterocycle. Additional deprotection steps can be included when appropriate. The optional functional group (e.g., an amine), when present can be further elaborated by, for example, alkylation or cyclo-alkylation.

Example 3. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |

| (i) Tablet 1 | mg/tablet |
|---|---|
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt.% |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Composition X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

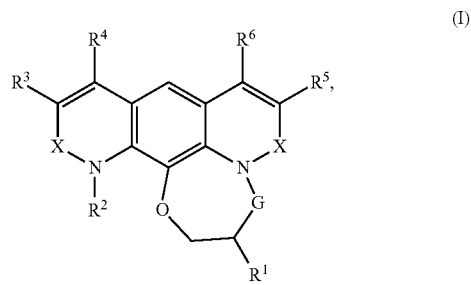

or a salt or solvate thereof;
wherein
G is a direct bond or $CH_2$;
X is $C\!=\!O$;

$R^1$ is H, —($C_1$-$C_6$)alkyl, —$OR^A$, —$SR^A$, —S(=O)$_2$N($R^A$)$_2$, —N($R^A$)$_2$, —($C_1$-$C_5$)alkyl-$OR^A$, —($C_1$-$C_5$)alkyl-$SR^A$, —($C_1$-$C_5$)alkyl-S(=O)$_2$N($R^A$)$_2$, —($C_1$-$C_5$)—N($R^A$)$_2$, or —($C_1$-$C_5$)alkyl-C(=O)$R^B$;

$R^2$ is H, —($C_1$-$C_6$)alkyl, or —($C_3$-$C_6$)cycloalkyl;

$R^3$ and $R^4$ are each independently H, —($C_1$-$C_6$)alkyl, or $R^3$ and $R^4$ taken together form a cycloalkyl or an aryl;

$R^5$ is H;

$R^6$ is H or —($C_1$-$C_6$)alkyl;

$R^A$ is H, —($C_1$-$C_6$)alkyl, —($C_3$-$C_6$)cycloalkyl, or —C(=O)$R^B$; and $R^B$ is H, —($C_1$-$C_6$)alkyl, —OH, or —NH$_2$;

wherein each —($C_1$-$C_6$)alkyl, —($C_3$-$C_6$)cycloalkyl and aryl is optionally substituted with one or more substituents and optionally both $R^A$ in the moiety N($R^A$)$_2$ taken together form a 5- or 6-membered heterocycle; and the compound of Formula I is not the compound:

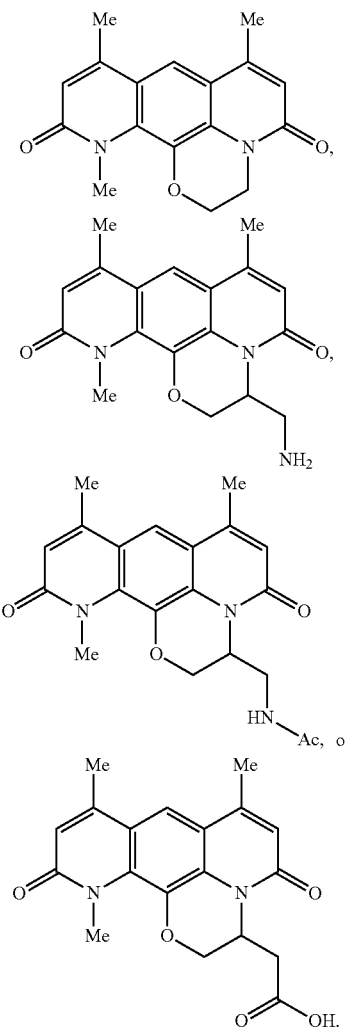

2. The compound of claim 1 wherein $R^1$ is H, —CH$_2$OH, —CH$_2$C(=O)OH, —CH$_2$NH$_2$, —CH$_2$-(pyrrolidine), —CH$_2$-(piperidine), —CH$_2$-(piperazine), —CH$_2$-(morpholine), —CH$_2$-(imidazole), —CH$_2$-(triazole), or —CH$_2$-(tetrazole).

3. A compound of Formula II:

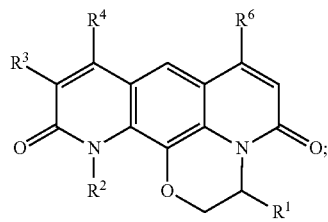

or a salt or solvate thereof, wherein $R^1$ is H, —($C_1$-$C_6$)alkyl, —$OR^A$, —$SR^A$, —S(=O)$_2$N($R^A$)$_2$, —N($R^A$)$_2$, —($C_1$-$C_5$)alkyl-$OR^A$, —($C_1$-$C_5$)alkyl-$SR^A$, —($C_1$-$C_5$)alkyl-S(=O)$_2$N($R^A$)$_2$, —($C_1$-$C_5$)—N($R^A$)$_2$, or —($C_1$-$C_5$)alkyl-C(=O)$R^B$;

$R^2$ is —($C_3$-$C_6$)cycloalkyl;

$R^3$ and $R^4$ are each independently H, —($C_1$-$C_6$)alkyl, or $R^3$ and $R^4$ taken together form a cycloalkyl or an aryl;

$R^6$ is H, —($C_1$-$C_6$)alkyl;

$R^A$ is H, —($C_1$-$C_6$)alkyl, —($C_3$-$C_6$)cycloalkyl, or —C(=O)$R^B$; and $R^B$ is H, —($C_1$-$C_6$)alkyl, —OH, or —NH$_7$;

wherein each —($C_1$-$C_6$)alkyl, —($C_3$-$C_6$)cycloalkyl and aryl is optionally substituted with one or more substituents and optionally both $R^A$ in the moiety N($R^A$)$_2$ taken together form a 5- or 6-membered heterocycle.

4. The compound of claim 1 wherein the compound is a compound of Formula III:

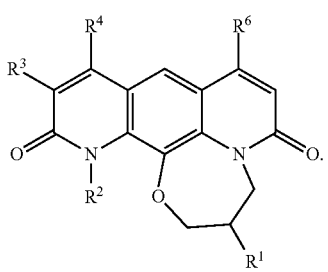

5. The compound of claim 1 wherein $R^1$ is not H and the compound is the (R)-enantiomer or the (S)-enantiomer.

6. The compound of claim 1 wherein $R^2$ and $R^6$ are —($C_1$-$C_6$)alkyl.

7. The compound of claim 6 wherein $R^4$ is —($C_1$-$C_6$)alkyl.

8. The compound of claim 1 wherein $R^3$ and $R^4$ taken together form a cycloalkyl or an aryl.

9. The compound of claim 1 wherein the compound is a compound of Formula IV:
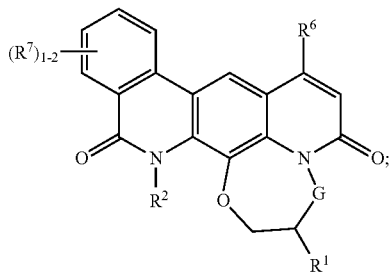
(IV)
wherein each $R^7$ is independently H, halo, —($C_1$-$C_6$) alkyl, —$OR^A$, —$SR^A$, —$N(R^A)_2$, —C(=O)$R^B$, —C(=O)N($R^A$)$_2$, or —S(=O)$_2$N($R^A$)$_2$.
10. The compound of claim 9 wherein the compound is a compound of Formula V:
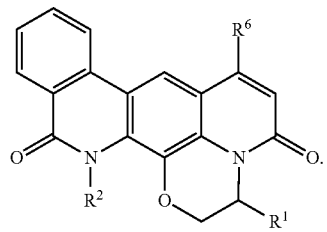
(V)
11. A compound selected from any one of compounds C1-C20:
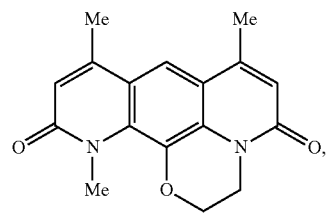
C1
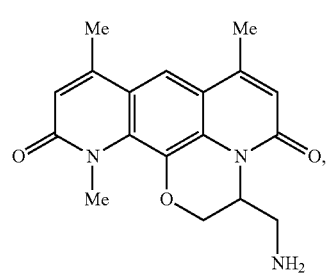
C2
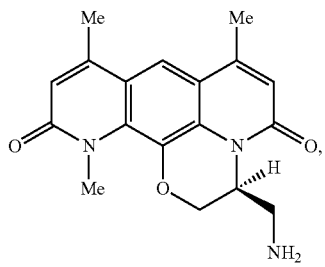
C3
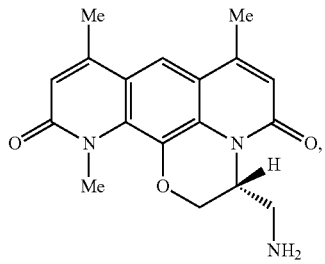
C4
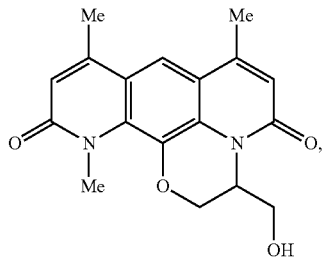
C5
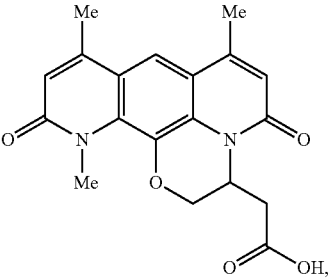
C6
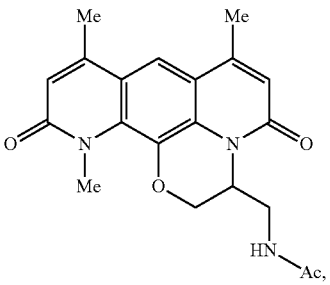
C7
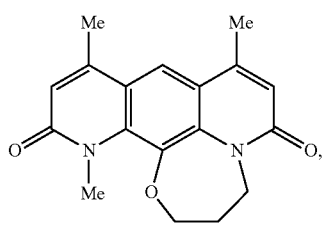
C8

C9
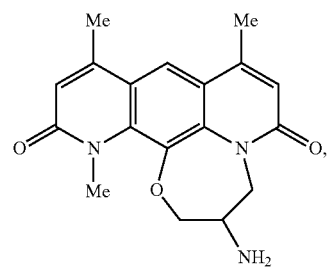
C10
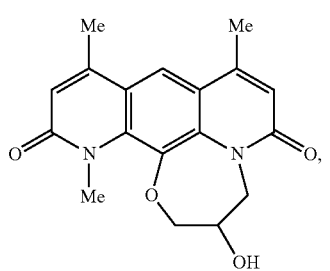
C11
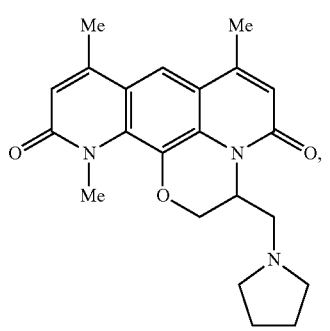
C12
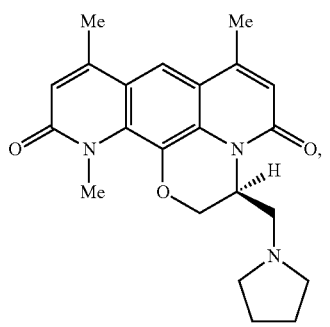
C13
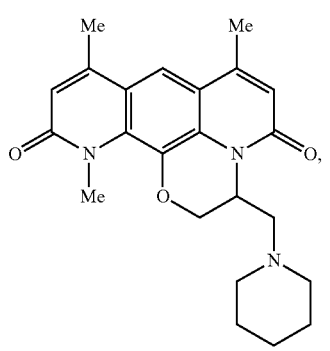
C14
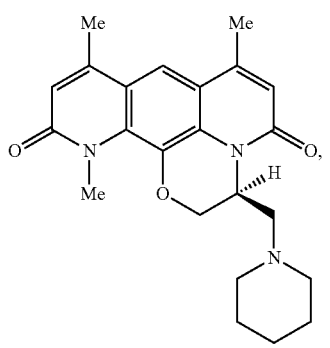
C15
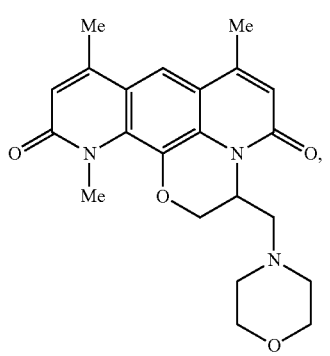
C16
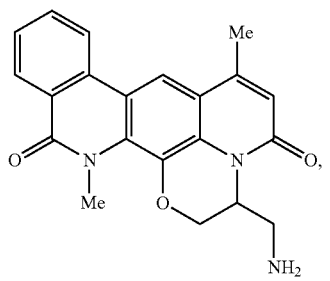
C17
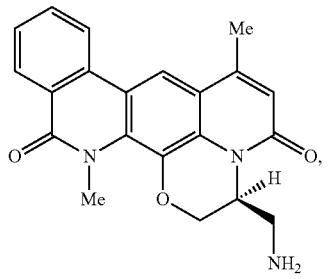
C18
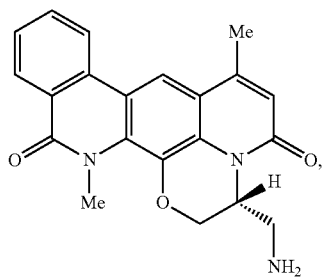

-continued

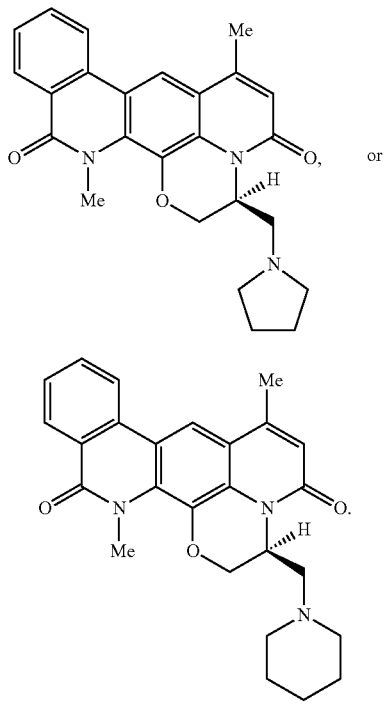

12. A pharmaceutical composition comprising a compound of claim 11 in combination with a pharmaceutically acceptable diluent, carrier, excipient, or buffer.

13. The compound of claim 1 wherein the compound is a compound of Formula II:

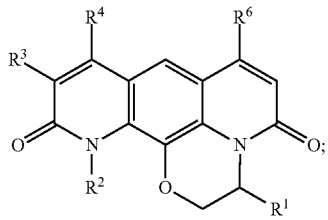

(II)

wherein $R^1$ is —$(C_1-C_6)$alkyl, —$OR^A$, —$SR^A$, —$S(=O)_2N(R^A)_2$, —$N(R^A)_2$, —$(C_1-C_5)$alkyl-$OR^A$, —$(C_1-C_5)$alkyl-$SR^A$, —$(C_1-C_5)$alkyl-$S(=O)_2N(R^A)_2$, or —$(C_1-C_5)$alkyl-$C(=O)R^B$; and $R^2$ is H or —$(C_1-C_6)$alkyl.

* * * * *

UNITED STATES PATENT AND TRADEMARK OFFICE
CERTIFICATE OF CORRECTION

PATENT NO. : 11,274,106 B2
APPLICATION NO. : 16/624335
DATED : March 15, 2022
INVENTOR(S) : Paul J. Hergenrother et al.

Page 1 of 1

It is certified that error appears in the above-identified patent and that said Letters Patent is hereby corrected as shown below:

In the Claims

Claim 3, at Column 66, Line 34, please delete "*NH$_7$*" and insert -- *NH$_2$* -- therefor.

Signed and Sealed this
Twenty-sixth Day of April, 2022

Katherine Kelly Vidal
*Director of the United States Patent and Trademark Office*